United States Patent
Sugaya et al.

(10) Patent No.: US 10,981,960 B2
(45) Date of Patent: Apr. 20, 2021

(54) LIVER-TYPE FATTY ACID-BINDING PROTEIN STANDARD, METHOD FOR EVALUATING STANDARD, METHOD FOR REGULATING VARIATION RANGE OF MEASURED VALUE CAUSED BY LIVER-TYPE FATTY ACID-BINDING PROTEIN IN MEASUREMENT USING STANDARD, LIVER-TYPE FATTY ACID-BINDING PROTEIN, DNA ENCODING PROTEIN, CELL TRANSFORMED BY DNA, METHOD OF PRODUCING PROTEIN, METHOD OF DRAWING CALIBRATION CURVE FOR LIVER-TYPE FATTY ACID-BINDING PROTEIN, AND METHOD OF QUANTIFYING PROTEIN

(71) Applicant: CMIC HOLDINGS CO., LTD., Tokyo (JP)

(72) Inventors: Takeshi Sugaya, Tokyo (JP); Masateru Okazaki, Tokyo (JP); Tsuyoshi Oikawa, Tokyo (JP)

(73) Assignee: CMIC HOLDINGS CO., LTD., Tokyo (JP)

( * ) Notice: Subject to any disclaimer, the term of this patent is extended or adjusted under 35 U.S.C. 154(b) by 0 days.

(21) Appl. No.: 16/087,333

(22) PCT Filed: Jun. 15, 2017

(86) PCT No.: PCT/JP2017/022209
§ 371 (c)(1),
(2) Date: Sep. 21, 2018

(87) PCT Pub. No.: WO2017/217514
PCT Pub. Date: Dec. 21, 2017

(65) Prior Publication Data
US 2019/0359663 A1 Nov. 28, 2019

(30) Foreign Application Priority Data

Jun. 16, 2016 (JP) .............................. JP2016-120073
Dec. 19, 2016 (JP) .............................. JP2016-246001

(51) Int. Cl.
*C07K 14/47* (2006.01)
*G01N 33/68* (2006.01)

(52) U.S. Cl.
CPC ............. *C07K 14/47* (2013.01); *G01N 33/68* (2013.01)

(58) Field of Classification Search
None
See application file for complete search history.

(56) References Cited

U.S. PATENT DOCUMENTS

| 7,592,148 B1 | 9/2009 | Yamanouchi et al. |
| 2012/0135433 A1 | 5/2012 | Sugaya et al. |
| 2013/0122530 A1 | 5/2013 | Hess et al. |

FOREIGN PATENT DOCUMENTS

| JP | 08-304395 | 11/1996 |
| JP | 8-304395 | 11/1996 |
| JP | 11-242026 A | 9/1999 |
| JP | 6059388 | 1/2017 |
| JP | 6174778 | 8/2017 |
| JP | 6218983 | 10/2017 |
| WO | 2011/007823 | 1/2011 |

OTHER PUBLICATIONS

Ek Ba etal. Fatty Acid Binding Proteins Reduce 15-lipoxygenase-inducedoxygenation of linoleic acid and arachidonic acid. 1997. Biochimica et Biophysica Acta 1346:75-85 (Year: 1997).*
NP_036688. Fatty acid binding protein, liver [*Rattus norvegicus*], 2014. Genbank. p. 1-3 (Year: 2014).*
NP_001434. Fatty acid binding protein, liver [*Homo sapiens*], 2015. Genbank. p. 1-3 (Year: 2015).*
Marini I et al. Chaperone-like features of bovine serum albumin: a comparison with alpha-crystallin. 2005. Cell. Mol. Life Sci. 62. 3092-3099. (Year: 2005).*
Database, Fatty acid-binding protein, liver [*Rattus norvegicus*]—Protein—NCBI [online], http://www.ncbi.nlm.nih.gov/protein/NP_036688.1, retrieved Jul. 12, 2016.

(Continued)

*Primary Examiner* — Paul J Holland
(74) *Attorney, Agent, or Firm* — Wenderoth, Lind & Ponack, L.L.P.

(57) ABSTRACT

The purpose of the present invention is to provide: a liver-type fatty acid-binding protein standard by which, in a measurement using a specifically binding substance, the range of variation of a measured value caused by a liver-type fatty acid-binding protein can be narrowed; a method of evaluating the standard; a method of drawing a calibration curve of a liver-type fatty acid-binding protein; and a method of quantifying the protein. A liver-type fatty acid-binding protein standard in which a coefficient of change in oxidation, said coefficient being represented by the ratio of a measured value obtained by using a liver-type fatty acid-binding protein standard having been subjected to an oxidation treatment with 10 mM of an oxidant for 1 hour at 25° C. to a measured value obtained by using the liver-type fatty acid-binding protein standard not subjected to the oxidation treatment, is set to 1.4 or less; a liver-type fatty acid-binding protein to be used in the standard; a DNA encoding the protein; a cell transformed by the DNA; a method of producing the protein; a method of evaluating the standard; a method of regulating the variation range of a measured value in a measurement using the standard; a method of drawing a calibration curve for the protein; and a method of quantifying the protein.

14 Claims, 24 Drawing Sheets

Specification includes a Sequence Listing.

(56) References Cited

OTHER PUBLICATIONS

Ghesquière et al., "Proteomics Methods to Study Methionine Oxidation", Mass Spectrometry Reviews, 2014, vol. 33, pp. 147-156.
Le et al., "Analysis of Methionine/Selenomethionime Oxidation and Methionine Sulfoxide Reductase Function Using Methionine-Rich Proteins and Antibodies against Their Oxidized Forms", Biochemistry, 2008, vol. 47, pp. 6685-6694.
Ludlow et al., "Development of a new antibody to the human inhibin/activin βB subunit and its application to improved inhibin B ELISAs", Journal of Immunological Methods, 2008, vol. 329, pp. 102-111.
Wehr et al., "Wanted and wanting: Antibody against methionine sulfoxide", Free Radical Biology and Medicine, 2012, vol. 53, pp. 1222-1225.
Pan et al., "Comparative Oxidation Studies of Methionine Residues Reflect a Structural Effect on Chemical Kinetics in rhG-CSF", Biochemistry, 2006, vol. 45, pp. 15430-15443.
Rolf et al., "Analysis of the ligand binding properties of recombinant bovine liver-type fatty acid binding protein", Biochemica et Biophysica Acta, 1995, vol. 1259, pp. 245-253.
Furuhashi et al., "Fatty acid-binding, proteins: role in metabolic diseases and potential as drug targets", Nat. Rev. Drug Discov., 2008, vol. 7(6), pp. 489-503.
Kamijo et al., "Urinary fatty acid-binding protein as a new clinical marker of the progression of chronic renal disease", J Lab Clin Med, 2004, vol. 143, pp. 23-30.
Cai et al., "Solution Structure and Backbone Dynamics of Human Liver Fatty Acid Binding Protein: Fatty Acid Binding Revisited", Biophysical Journal, 2012 vol. 102, pp. 2585-2594.
Veerkamp et al., "Structural and Functional Aspects of Cytosolic Fatty Acid-Binding Proteins", Prostaglandins Leukot Essent Fatty Acids, 1993, vol. 49, pp. 887-906.
Zimmerman et al., "Ligand specificity and conformational stability of human fatty acid-binding proteins", The International Journal of Biochemistry & Cell Biology, 2001, vol. 33, pp. 865-876.
Norris et al., "Very long chain n-3 and n-6 polyunsaturated fatty acids bind strongly to liver fatty acid-binding protein", Journal of Lipid Research, 2002, vol. 43, pp. 646-653.
Raza et al., "Specific High Affinity Binding of Lipoxygenase Metabolites of Arachidonic Acid by Liver Fatty Acid Binding Protein", Biochemical and Biophysical Research Communications, 1989, vol. 161, No. 2, pp. 448-455.
Renischem L-FABP ELISA TMB Kit *Instruction leaflet for Renapuro L-FABP Test TMB, 3rd edition, Revised Jun. 2017.
Extended European Search Report dated Feb. 20, 2019 in corresponding EP Patent Application No. 17813408.6.
Thompson et al., "The Crystal Structure of the Liver Fatty Acid-Binding Protein. A complex with two bound oleates", Journal of Biological Chemistry, 1997 vol. 272, No. 11, pp. 7140-7150.
"Renishem L-FABP ELISA TMB Kit, a kit for quantitative determination of human LFABP in urine", CMIC Holding Co., Tokyo, Aug. 2015, pp. 1-4, XP002788456, retrieved from the Internet: URL:https://www.fabp.jp/eng/pdf/161114_tmbinst.pdf.
Written Opinion of International Searching Authority dated Sep. 19, 2017 in corresponding International (PCT) Application No. PCT/JP2017/022209.
Maatman et al., "Expression of human liver fatty acid-binding protein in *Escherichia coli* and comparative analysis of its binding characteristics with muscle fatty acid-binding protein", Biochem. Biophys. Acta., 1994, vol. 1214, No. 1, pp. 1-10.
Kim et al., "Comparing the effect on protein stability of methionine oxidation versus mutagenesis: steps toward engineering oxidative resistance in proteins", Protein Engineering, 2001, vol. 14, No. 5, pp. 343-347.
Manning et al., "Stability of Protein Pharmaceuticals: An Update", Pharmaceutical Research, 2010, vol. 27, No. 4, pp. 544-575.
Yan et al., "Molecular mechanism of recombinant liver fatty acid binding protein's antioxidant activity", J. Lipid Res., 2009, vol. 50, pp. 2445-2454.
Renapro L-FABP Test TMB, 3rd edition, CIMIC Holdings CO., Ltd., 2015, in particular, "Shape, Structure, etc.", "Intended Use", "Measurement Principle", and "Usage, Dosage".
International Search Report dated Sep. 19, 2017 in International (PCT) Application No. PCT/JP2017/022209.
Office Action dated Mar. 19, 2019 in corresponding Chinese Patent Application No. 201780019737.X, with Machine Translation.
Notification of Reasons for Refusal dated Mar. 26, 2019 in Japanese Patent Application No. 2018-524015.
L-FABP [*Homo sapiens*] Genbank : AAA52419, 1994, 1 page.
Song Wei, "Studies on the Interaction of Liver-type Fatty Acid Binding Proteins with Lipophilic Drugs", Chinese Excellent Masterchars Degree Dissertation, Full-text Database Medical Science and Technology Series, 2009, No. 12, pp. E079-68, with Concise Explanation (p. 3).

* cited by examiner

|  | MEASUREMENT RESULTS | DIFFERENCE FROM *THEORETICAL MOLECULAR WEIGHT |
|---|---|---|
| OXIDIZED TYPE L-FABP | 14257.2 | 49.2 |
|  | 14240.7 | 32.7 |
| NON-OXIDIZED TYPE L-FABP | 14207.3 | -0.7 |

*THEORETICAL MOLECULAR WEIGHT : 14208

FIG. 5A

```
          10         20         30         40
MSFSGKYQLQ SQENFEAFMK AIGLPEELIQ KGKDIKGVSE
IVQNGKHFKF TITAGSKVIQ NEFTVGEECE LETMTGEKVK
TVVQLEGDNK LVTTFKNIKS VTELNGDIIT NTMTLGDIVF
KRISKRI  (SEQ ID NO:1)
```

FIG. 5B

| No. | SEQUENCE | SUSPECTED MOLECULAR WEIGHT | |
|---|---|---|---|
| 1 | MSFSGK  (SEQ ID NO:5) | 655.77 | |
| 2 | YQLQSQENFEAFMK  (SEQ ID NO:6) | 1762.95 | |
| 3 | AIGLPEELIQK  (SEQ ID NO:7) | 1210.44 | |
| 4 | GK | 203.24 | |
| 5 | DIK | 374.44 | |
| 6 | GVSEIVQNGK  (SEQ ID NO:8) | 1030.15 | |
| 7 | HFK | 430.51 | |
| 8 | FTITAGSK  (SEQ ID NO:9) | 823.94 | |
| 9 | VIQNEFTVGEECELETMTGEK | 2386.63 | (SEQ ID NO:10) |
| 10 | VK | 245.32 | |
| 11 | TVVQLEGDNK  (SEQ ID NO:11) | 1102.21 | |
| 12 | LVTTFK  (SEQ ID NO:12) | 707.87 | |
| 13 | NIK | 373.45 | |
| 14 | SVTELNGDIITNTMTLGDIVFK | 2381.72 | (SEQ ID NO:13) |
| 15 | R | 174.2 | |
| 16 | ISK | 346.43 | |
| 17 | R | 174.2 | |
| 18 | I | 131.17 | |

SEQUENCE LISTING

<160> NUMBER OF SEQ ID NOS: 13

<210> SEQ ID NO 1
<211> LENGTH: 127
<212> TYPE: PRT
<213> ORGANISM: Homo sapiens
<220> FEATURE:
<221> NAME/KEY: MOD_RES
<222> LOCATION: (19)..(19)
<223> OTHER INFORMATION: Oxidation site of -L-FABP
<220> FEATURE:
<221> NAME/KEY: MOD_RES
<222> LOCATION: (74)..(74)
<223> OTHER INFORMATION: Oxidation site of -L-FABP
<220> FEATURE:
<221> NAME/KEY: MOD_RES
<222> LOCATION: (113)..(113)
<223> OTHER INFORMATION: Oxidation site of -L-FABP

<400> SEQUENCE: 1

Met Ser Phe Ser Gly Lys Tyr Gln Leu Gln Ser Gln Glu Asn Phe Glu
1               5                   10                  15

Ala Phe Met Lys Ala Ile Gly Leu Pro Glu Glu Leu Ile Gln Lys Gly
            20                  25                  30

Lys Asp Ile Lys Gly Val Ser Glu Ile Val Gln Asn Gly Lys His Phe
        35                  40                  45

Lys Phe Thr Ile Thr Ala Gly Ser Lys Val Ile Gln Asn Glu Phe Thr
    50                  55                  60

Val Gly Glu Glu Cys Glu Leu Glu Thr Met Thr Gly Glu Lys Val Lys
65                  70                  75                  80

Thr Val Val Gln Leu Glu Gly Asp Asn Lys Leu Val Thr Thr Phe Lys
                85                  90                  95

Asn Ile Lys Ser Val Thr Glu Leu Asn Gly Asp Ile Ile Thr Asn Thr
            100                 105                 110

Met Thr Leu Gly Asp Ile Val Phe Lys Arg Ile Ser Lys Arg Ile
        115                 120                 125

<210> SEQ ID NO 2
<211> LENGTH: 127
<212> TYPE: PRT
<213> ORGANISM: Artificial Sequence
<220> FEATURE:
<223> OTHER INFORMATION: Mutant of L-FABP protein
<220> FEATURE:
<221> NAME/KEY: MUTAGEN
<222> LOCATION: (19)..(19)
<223> OTHER INFORMATION: Mutation of methionine to leucine
<220> FEATURE:
<221> NAME/KEY: MUTAGEN
<222> LOCATION: (74)..(74)
<223> OTHER INFORMATION: Mutation of methionine to leucine
<220> FEATURE:
<221> NAME/KEY: MUTAGEN
<222> LOCATION: (113)..(113)
<223> OTHER INFORMATION: Mutation of methionine to leucine

<400> SEQUENCE: 2

Met Ser Phe Ser Gly Lys Tyr Gln Leu Gln Ser Gln Glu Asn Phe Glu
1               5                   10                  15

Ala Phe Leu Lys Ala Ile Gly Leu Pro Glu Glu Leu Ile Gln Lys Gly
            20                  25                  30

Lys Asp Ile Lys Gly Val Ser Glu Ile Val Gln Asn Gly Lys His Phe
        35                  40                  45

Lys Phe Thr Ile Thr Ala Gly Ser Lys Val Ile Gln Asn Glu Phe Thr
    50                  55                  60

```
Val Gly Glu Glu Cys Glu Leu Glu Thr Leu Thr Gly Glu Lys Val Lys
 65                  70                  75                  80

Thr Val Val Gln Leu Glu Gly Asp Asn Lys Leu Val Thr Thr Phe Lys
                 85                  90                  95

Asn Ile Lys Ser Val Thr Glu Leu Asn Gly Asp Ile Ile Thr Asn Thr
            100                 105                 110

Leu Thr Leu Gly Asp Ile Val Phe Lys Arg Ile Ser Lys Arg Ile
        115                 120                 125
```

<210> SEQ ID NO 3
<211> LENGTH: 384
<212> TYPE: DNA
<213> ORGANISM: Artificial Sequence
<220> FEATURE:
<223> OTHER INFORMATION: Mutant of L-FABP protein
<220> FEATURE:
<221> NAME/KEY: CDS
<222> LOCATION: (1)..(384)

<400> SEQUENCE: 3

```
atg tcc ttc tct ggc aag tac cag ctg cag tcc cag gaa aac ttc gag    48
Met Ser Phe Ser Gly Lys Tyr Gln Leu Gln Ser Gln Glu Asn Phe Glu
1               5                   10                  15 gca ttc ctc aaa gct atc ggt ctg cca gaa gag ctc atc cag aag ggc    96
Ala Phe Leu Lys Ala Ile Gly Leu Pro Glu Glu Leu Ile Gln Lys Gly
            20                  25                  30 aaa gat att aag ggt gtt tcc gaa atc gtg cag aac ggc aag cac ttc   144
Lys Asp Ile Lys Gly Val Ser Glu Ile Val Gln Asn Gly Lys His Phe
        35                  40                  45 aaa ttc acc att acc gca ggt tct aag gtc atc cag aac gag ttc acc   192
Lys Phe Thr Ile Thr Ala Gly Ser Lys Val Ile Gln Asn Glu Phe Thr
    50                  55                  60 gtt ggc gaa gag tgc gaa ctt gag acc ttg acc ggt gaa aag gtt aaa   240
Val Gly Glu Glu Cys Glu Leu Glu Thr Leu Thr Gly Glu Lys Val Lys
65                  70                  75                  80 acc gtg gtc cag ctt gag ggc gac aac aag ttg gtg acc acc ttc aag   288
Thr Val Val Gln Leu Glu Gly Asp Asn Lys Leu Val Thr Thr Phe Lys
                85                  90                  95 aac att aaa tcc gtc acc gaa ctg aac ggc gat atc att acc aac acc   336
Asn Ile Lys Ser Val Thr Glu Leu Asn Gly Asp Ile Ile Thr Asn Thr
            100                 105                 110 ctg acc ctc ggt gac atc gtg ttc aag cgc atc tct aaa cgt att taa   384
Leu Thr Leu Gly Asp Ile Val Phe Lys Arg Ile Ser Lys Arg Ile
        115                 120                 125
```

<210> SEQ ID NO 4
<211> LENGTH: 127
<212> TYPE: PRT
<213> ORGANISM: Artificial Sequence
<220> FEATURE:
<223> OTHER INFORMATION: Synthetic Construct

<400> SEQUENCE: 4

```
Met Ser Phe Ser Gly Lys Tyr Gln Leu Gln Ser Gln Glu Asn Phe Glu
1               5                   10                  15

Ala Phe Leu Lys Ala Ile Gly Leu Pro Glu Glu Leu Ile Gln Lys Gly
            20                  25                  30

Lys Asp Ile Lys Gly Val Ser Glu Ile Val Gln Asn Gly Lys His Phe
        35                  40                  45

Lys Phe Thr Ile Thr Ala Gly Ser Lys Val Ile Gln Asn Glu Phe Thr
    50                  55                  60
```

```
Val Gly Glu Glu Cys Glu Leu Glu Thr Leu Thr Gly Glu Lys Val Lys
 65                  70                  75                  80

Thr Val Val Gln Leu Glu Gly Asp Asn Lys Leu Val Thr Thr Phe Lys
                 85                  90                  95

Asn Ile Lys Ser Val Thr Glu Leu Asn Gly Asp Ile Ile Thr Asn Thr
            100                 105                 110

Leu Thr Leu Gly Asp Ile Val Phe Lys Arg Ile Ser Lys Arg Ile
        115                 120                 125
```

<210> SEQ ID NO 5
<211> LENGTH: 6
<212> TYPE: PRT
<213> ORGANISM: Artificial Sequence
<220> FEATURE:
<223> OTHER INFORMATION: Fragment of L-FABP protein

<400> SEQUENCE: 5

```
Met Ser Phe Ser Gly Lys
1               5
```

<210> SEQ ID NO 6
<211> LENGTH: 14
<212> TYPE: PRT
<213> ORGANISM: Artificial Sequence
<220> FEATURE:
<223> OTHER INFORMATION: Fragment of L-FABP protein

<400> SEQUENCE: 6

```
Tyr Gln Leu Gln Ser Gln Glu Asn Phe Glu Ala Phe Met Lys
1               5                   10
```

<210> SEQ ID NO 7
<211> LENGTH: 11
<212> TYPE: PRT
<213> ORGANISM: Artificial Sequence
<220> FEATURE:
<223> OTHER INFORMATION: Fragment of L-FABP protein

<400> SEQUENCE: 7

```
Ala Ile Gly Leu Pro Glu Glu Leu Ile Gln Lys
1               5                   10
```

<210> SEQ ID NO 8
<211> LENGTH: 10
<212> TYPE: PRT
<213> ORGANISM: Artificial Sequence
<220> FEATURE:
<223> OTHER INFORMATION: Fragment of L-FABP protein

<400> SEQUENCE: 8

```
Gly Val Ser Glu Ile Val Gln Asn Gly Lys
1               5                   10
```

<210> SEQ ID NO 9
<211> LENGTH: 8
<212> TYPE: PRT
<213> ORGANISM: Artificial Sequence
<220> FEATURE:
<223> OTHER INFORMATION: Fragment of L-FABP protein

<400> SEQUENCE: 9

```
Phe Thr Ile Thr Ala Gly Ser Lys
1               5
```

```
<210> SEQ ID NO 10
<211> LENGTH: 21
<212> TYPE: PRT
<213> ORGANISM: Artificial Sequence
<220> FEATURE:
<223> OTHER INFORMATION: Fragment of L-FABP protein

<400> SEQUENCE: 10

Val Ile Gln Asn Glu Phe Thr Val Gly Glu Glu Cys Glu Leu Glu Thr
1               5                   10                  15

Met Thr Gly Glu Lys
            20

<210> SEQ ID NO 11
<211> LENGTH: 10
<212> TYPE: PRT
<213> ORGANISM: Artificial Sequence
<220> FEATURE:
<223> OTHER INFORMATION: Fragment of L-FABP protein

<400> SEQUENCE: 11

Thr Val Val Gln Leu Glu Gly Asp Asn Lys
1               5                   10

<210> SEQ ID NO 12
<211> LENGTH: 6
<212> TYPE: PRT
<213> ORGANISM: Artificial Sequence
<220> FEATURE:
<223> OTHER INFORMATION: Fragment of L-FABP protein

<400> SEQUENCE: 12

Leu Val Thr Thr Phe Lys
1               5

<210> SEQ ID NO 13
<211> LENGTH: 22
<212> TYPE: PRT
<213> ORGANISM: Artificial Sequence
<220> FEATURE:
<223> OTHER INFORMATION: Fragment of L-FABP protein

<400> SEQUENCE: 13

Ser Val Thr Glu Leu Asn Gly Asp Ile Ile Thr Asn Thr Met Thr Leu
1               5                   10                  15

Gly Asp Ile Val Phe Lys
            20
```

LIVER-TYPE FATTY ACID-BINDING PROTEIN STANDARD, METHOD FOR EVALUATING STANDARD, METHOD FOR REGULATING VARIATION RANGE OF MEASURED VALUE CAUSED BY LIVER-TYPE FATTY ACID-BINDING PROTEIN IN MEASUREMENT USING STANDARD, LIVER-TYPE FATTY ACID-BINDING PROTEIN, DNA ENCODING PROTEIN, CELL TRANSFORMED BY DNA, METHOD OF PRODUCING PROTEIN, METHOD OF DRAWING CALIBRATION CURVE FOR LIVER-TYPE FATTY ACID-BINDING PROTEIN, AND METHOD OF QUANTIFYING PROTEIN

TECHNICAL FIELD

The present invention relates to a liver-type fatty acid-binding protein standard (preparation) by which, in a measurement using a specifically binding substance, the variation range of a measured value attributed to liver-type fatty acid-binding protein can be narrowed; a method of evaluating the standard; a method of regulating the variation range of a measured value attributed to liver-type fatty acid-binding protein in a measurement using the standard; a liver-type fatty acid-binding protein; a DNA encoding the protein; a cell that has been transformed by the DNA; a method of producing the protein; a method of drawing a calibration curve for the liver-type fatty acid-binding protein; and a method of quantifying the protein.

BACKGROUND ART

Fatty Acid-Binding Proteins (hereinafter, also referred to as FABPs) are proteins having a molecular weight of about 14 kDa, which belong to the intracellular lipid-binding protein family, and it is known that the fatty acid-binding proteins reversibly bind to hydrophobic ligands including fatty acids and are responsible for the intracellular transport of the hydrophobic ligands (for example, Non-Patent Document 1). Among them, liver-type fatty acid-binding protein (L-type fatty acid-binding protein; hereinafter, also simply referred to as "L-FABP protein") is localized in the cytoplasm of proximal tubule cells in the liver and the kidneys, and the excretion of the protein in urine increases in response to ischemia and oxidative stress caused by tubular disorders (for example, Non-Patent Document 2). Therefore, examination of renal diseases is made possible by detecting renal tissue-derived L-FABP protein in urine (for example, Patent Document 1). Furthermore, as shown in FIG. 24, it is known that L-FABP protein is stabilized in the form in which a β-barrel structure having two sheets of antiparallel β-sheets running straight has a lid formed by two α-helices, and L-FABP protein binds to two molecules of a free fatty acid (for example, oleic acid) (PDB ID: 2LKK) (Non-Patent Document 3). L-FABP protein has a mechanism of transporting free fatty acids to mitochondria or peroxisomes and accelerating β-oxidation (Non-Patent Document 4). Regarding the binding affinity for fatty acid ligands, it has been reported that there is a tendency that the binding affinity increases as the carbon chain of a fatty acid is extended and the number of double bonds increases (Non-Patent Documents 5 and 6), and L-FABP protein has high binding affinity especially for peroxides (Non-Patent Document 7). In a report on a study of the antioxidative mechanism of L-FABP protein, it has been disclosed that methionine residues of rat L-FABP protein are oxidized by AAPH (Non-Patent Document 8).

Patent Document 1: Japanese Unexamined Patent Application, Publication No. H11-242026
Non-Patent Document 1: Furuhashi, M., et al.: Nat Rev Drug Discov, 7:489-503, 2008
Non-Patent Document 2: Kamijo, A. et al.: J Lab Clin Med, 143:23-30, 2004
Non-Patent Document 3: Cai, J. et al.: Biophys J, 102:2585-2594, 2012
Non-Patent Document 4: Veerkamp, J. H. et al.: Prostaglandins Leukot Essent Fatty Acids, 49:887-906, 1993
Non-Patent Document 5: Zimmerman, A. W. et al.: Int J Biochem Cell Biol, 33:865-876, 2001
Non-Patent Document 6: Norris, A. W., Spector, A. A.: J Lipid Res, 43:646-653, 2002
Non-Patent Document 7: Raza, H. et al.: Biochem Biophys Res Commun, 161:448-455, 1989
Non-Patent Document 8: Yan, J. et al.: J Lipid Res, 50:2445-2454, 2009

DISCLOSURE OF THE INVENTION

Problems to be Solved by the Invention

As an examination kit for detecting L-FABP protein such as described above, for example, an examination kit employing a sandwich ELISA method, in which two kinds of antibodies having different recognition sites for L-FABP protein are used in combination, has been developed. Here, FIG. 1 is a diagram showing the storage stability of L-FABP, and the graph in FIG. 1 represents the changes in the ELISA measured value depending on the number of days under storage in a case in which L-FABP is stored at 4° C., 25° C., or 37° C. (proportions (%) obtained by designating the ELISA measured value of a sample stored at −80° C. taken as 100). In regard to the examination kit employing a sandwich ELISA method, there has been a problem that in a conventional measurement standard substance (preparation) using recombinant L-FABP protein, when the L-FABP protein is stored for a long time period at a temperature higher than or equal to room temperature (25° C.), as shown in FIG. 1, the antibody binding capacity is changed, and thus, accurate measurement of L-FABP protein by an immunological technique utilizing an antigen-antibody reaction, such as an ELISA method, cannot be carried out. As such, due to the instability of L-FABP protein, stringent management is required for the production conditions or measurement environment for L-FABP protein standards, and the standards are required to be stored at low temperature, while further enhancement of operability and stability are desired.

The present invention was achieved in view of the circumstances described above, and it is an object of the invention to provide a liver-type fatty acid-binding protein standard by which, in a measurement using a specifically binding substance, the variation range of a measured value attributed to liver-type fatty acid-binding protein can be narrowed; a method of evaluating the standard; a method of regulating the variation range of a measured value attributed to liver-type fatty acid-binding protein in a measurement using the standard; a method of drawing a calibration curve for a liver-type fatty acid-binding protein; and a method of quantifying the protein.

Means for Solving the Problems

The inventors of the present invention conducted a thorough investigation in order to solve the problems described above, and as a result, the inventors found that L-FABP protein undergoes oxidative modification and structural change in methionine residues when subjected to treatment with 2,2'-azobis2-amidinopropane (hereinafter, abbreviated to AAPH), which is an oxidant, and as a result, the antibody binding capacity in ELISA is changed, while the ELISA measured value significantly fluctuates. Furthermore, the inventors also found that, surprisingly, even in the case of non-addition of AAPH ($H_2O$ is added), when the protein is caused to react for one hour at room temperature, the ELISA measured value increases, and there is an influence caused by air oxidation. Particularly, in regard to the regulation of the variation range of an ELISA measured value, the inventors found that among the methionines at positions 19, 74, and 113, the oxidation ratios of the methionines at positions 19 and 113 are dominant.

Furthermore, the inventors found that an L-FABP protein in which methionine residues in L-FABP protein have been changed to other amino acids by a technology for genetic modification, is stabilized without any change in the antibody binding capacity, even when subjected to an oxidation reaction, addition of fatty acids, or long-term storage at a temperature higher than or equal to room temperature. The present invention was finally completed based on the findings described above.

That is, the present invention is as follows. A first aspect of the present invention is a liver-type fatty acid-binding protein standard for which the coefficient of change in oxidation is set to 1.4 or less. A second aspect of the present invention is a liver-type fatty acid-binding protein standard including a liver-type fatty acid-binding protein, the liver-type fatty acid-binding protein comprising an amino acid sequence having at least 90% identity with SEQ ID NO:1 of the Sequence Listing and having one or more methionines at positions 19, 74, and 113 substituted by non-polar amino acids other than methionine, in which at least the methionine at position 19 has been substituted by a non-polar amino acid other than methionine. A third aspect of the present invention is a liver-type fatty acid-binding protein that is used for the liver-type fatty acid-binding protein standard according to the first aspect, the liver-type fatty acid-binding protein comprising an amino acid sequence having at least 90% identity with SEQ ID NO:1 of the Sequence Listing and having one or more methionines at positions 19, 74, and 113 substituted by non-polar amino acids other than methionine. A fourth aspect of the present invention is a DNA encoding the protein according to the third aspect. A fifth aspect of the present invention is a cell that has been transformed with the DNA according to the fourth aspect. A sixth aspect of the present invention is a method of producing a protein comprising a step of culturing the cell according to the fifth aspect and collecting the protein according to the third aspect.

A seventh aspect of the present invention is a liver-type fatty acid-binding protein standard including a liver-type fatty acid-binding protein, the liver-type fatty acid-binding protein comprising an amino acid sequence having at least 90% identity with SEQ ID NO:1 of the Sequence Listing, in which an oxidation ratio of methionine at position 19 is 30% or higher, or an oxidation ratio of methionine at position 113 is 70% or higher. An eighth aspect of the present invention is a liver-type fatty acid-binding protein standard comprising at least one fatty acid selected from the group consisting of arachidonic acid, oleic acid, 8-iso-prostaglandin $F_{2\alpha}$, and 2,3-dinor-8-iso-prostaglandin $F_{2\alpha}$ in an amount such that the coefficient of change in oxidation becomes 1.4 or less, and also comprising a liver-type fatty acid-binding protein comprising an amino acid sequence having at least 90% identity with SEQ ID NO:1 of the Sequence Listing.

A ninth aspect of the present invention is a method of evaluating a liver-type fatty acid-binding protein standard by using the coefficient of change in oxidation as an index. A tenth aspect of the present invention is a method of regulating the variation range of a measured value in a measurement using a liver-type fatty acid-binding protein standard, the method comprising at least any one selected from the group consisting of the following:

(1) substituting one or more methionines at positions 19, 74, and 113 of a liver-type fatty acid-binding protein comprising an amino acid sequence having at least 90% identity with SEQ ID NO:1 of the Sequence Listing, with non-polar amino acids other than methionine, and substituting at least methionine at position 19 with a non-polar amino acid other than methionine;

(2) adjusting the oxidation ratio of methionine at position 19 of a liver-type fatty acid-binding protein comprising an amino acid sequence having at least 90% identity with SEQ ID NO:1 of the Sequence Listing to 30% or higher, or adjusting the oxidation ratio of methionine at position 113 to 70% or higher; and (3) incorporating at least one fatty acid selected from the group consisting of arachidonic acid, oleic acid, 8-iso-prostaglandin $F_{2\alpha}$, and 2,3-dinor-8-iso-prostaglandin $F_{2\alpha}$, into the liver-type fatty acid-binding protein standard. An eleventh aspect of the present invention is a method of drawing a calibration curve for a liver-type fatty acid-binding protein using the liver-type fatty acid-binding protein standard according to any one of the first, second, seventh, and eighth aspects. A twelfth aspect of the present invention is a method of quantifying a liver-type fatty acid-binding protein in a sample using the calibration curve drawn by the method according to the eleventh aspect.

Effects of the Invention

According to the present invention, a liver-type fatty acid-binding protein standard by which, in a measurement using a specifically binding substance, the variation range of a measured value attributed to liver-type fatty acid-binding protein can be narrowed; a method of drawing a calibration curve for a liver-type fatty acid-binding protein; and a method of quantifying the protein can be provided. Since the liver-type fatty acid-binding protein standard of the present invention is such that any change in the antibody binding capacity caused by oxidation or the state of binding to a fatty acid can be regulated, the liver-type fatty acid-binding protein standard does not depend on the biological species of origin or the protein expression method. That is, the liver-type fatty acid-binding protein standard of the present invention can provide stability and general-purpose usability in view of the production conditions, storage conditions, and operability. Furthermore, in the method for evaluating a liver-type fatty acid-binding protein standard of the present invention, the degree of variation of the measured value of a liver-type fatty acid-binding protein caused by oxidation can be evaluated as a coefficient.

The liver-type fatty acid-binding protein standard of the present invention enables, in a measurement using a specifically binding substance (for example, an antibody), the variation range of a measured value attributed to liver-type fatty acid-binding protein to be narrowed, and thus, accurate detection or quantitative determination is made possible without depending on temperature or the degree of oxidation. Furthermore, since the liver-type fatty acid-binding protein standard of the present invention enables, in a measurement using a specifically binding substance, the variation range of a measured value attributed to liver-type fatty acid-binding protein to be narrowed, production and management of liver-type fatty acid-binding protein as a standard substance for measurement or a substance for accuracy management is facilitated, and it is expected to enhance the operability and general-purpose usability of measurement in an immunological technique.

BRIEF DESCRIPTION OF THE DRAWINGS

FIG. 5(a) is a diagram showing the amino acid sequence of human L-FABP protein set forth in SEQ ID NO:1; and FIG. 5(b) is a diagram showing the suspected molecular weights of various peptide fragments that can be produced by trypsin digestion of human L-FABP protein.

PREFERRED MODE FOR CARRYING OUT THE INVENTION

Figure 1:
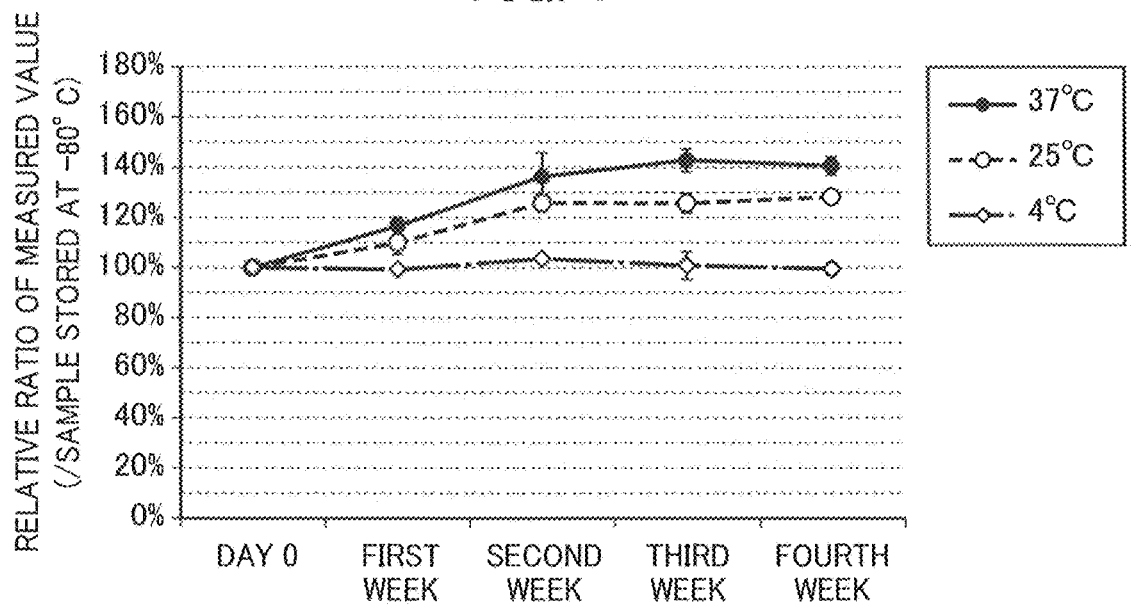
FIG. 1 is a diagram showing the storage stability of L-FABP protein.

In the following description, embodiments of the present invention will be described in detail; however, the present invention is not intended to be limited to the following embodiments, and the present invention can be carried out by applying appropriate modifications within the intended scope of the present invention.

<<Liver-Type Fatty Acid-Binding Protein Standard>>

According to the present specification, the term "standard" means substances comprising, as representative examples, a standard substance for measurement (calibrator) and a substance for accuracy management (control), and also comprising all standard products such as a reference standard material, a working standard material, a manufacturer's product calibration material, a standard material for diagnosis, and a standard material for calibration, as well as material for product quality control (Yoshiaki Iizuka et al., "Current status of metrological traceability and measurement uncertainty in clinical laboratories", Seibutsu Shiryo Bunseki (Journal of Analytical Bio-Science), Vol. 34, No. 3 (2011), pp. 179-188; Standard products and standard substances in Japanese Pharmacopeia, 2009 JCCLS (Japanese Committee for Clinical Laboratory Standards) Terminology Committee terms (English) and Japanese translations thereof (suggestions) No. 226).

<Liver-Type Fatty Acid-Binding Protein Standard Having Coefficient of Change in Oxidation Set to 1.4 or Less>

The liver-type fatty acid-binding protein standard according to the first aspect comprises a liver-type fatty acid-binding protein having a coefficient of change in oxidation set to 1.4 or less, the coefficient of change in oxidation being represented by the ratio of a measured value of an oxidation-treated liver-type fatty acid-binding protein standard, which has been subjected to an oxidation treatment for one hour at 25° C. using a 10 mM oxidant, with respect to the measured value of a non-oxidation-treated liver-type fatty acid-binding protein standard. When the coefficient of change in oxidation is 1.4 or less, variation of a measured value caused by oxidation can be regulated. The liver-type fatty acid-binding protein standard according to the first aspect is preferably a liver-type fatty acid-binding protein standard supplied to sales, from the viewpoint of being utilized for practical use and commercial use.

In the present specification and the claims, the coefficient of change in oxidation refers to the ratio of a measured value obtained by performing an oxidation treatment for one hour at room temperature (25° C.) using a 10 mM oxidant (for example, AAPH) and making a measurement using the oxidation-treated liver-type fatty acid-binding protein standard, with respect to the measured value obtained using a non-oxidation-treated liver-type fatty acid-binding protein standard. The coefficient of change in oxidation is preferably the ratio (for example, light absorbance ratio (OD ratio) represented by the following formula) of a measured value (for example, labeling intensity) obtained by performing an oxidation treatment for one hour at room temperature (25° C.) using 10 mM AAPH and performing a measurement using the oxidation-treated liver-type fatty acid-binding protein standard, with respect to the measured value of a non-oxidation-treated liver-type fatty acid-binding protein standard.

OD value obtained using the oxidation-treated liver-type fatty acid-binding protein standard/OD value obtained using the non-oxidation-treated liver-type fatty acid-binding protein standard In regard to the liver-type fatty acid-binding protein standard according to the first aspect, the coefficient of change in oxidation is preferably 1.3 or less. In regard to the liver-type fatty acid-binding protein standard according to the first aspect, the lower limit of the coefficient of change in oxidation is not particularly limited as long as the effects of the present invention are not impaired; however, for example, the lower limit may be 0.8 or more, preferably 0.9 or more, and more preferably 1.0 or more.

(Liver-Type Fatty Acid-Binding Protein Standard According to Second Aspect)

The liver-type fatty acid-binding protein standard according to the second aspect includes a mutant liver-type fatty acid-binding protein according to the following third aspect, in which the liver-type fatty acid-binding protein comprises an amino acid sequence having at least 90% identity with SEQ ID NO:1 of the Sequence Listing one or more methionines at positions 19, 74, and 113 have been substituted by non-polar amino acids other than methionine. Since the liver-type fatty acid-binding protein standard comprises the mutant liver-type fatty acid-binding protein described below, the variation in the binding capacity caused by a specifically binding substance can be regulated. The liver-type fatty acid-binding protein standard according to the second aspect may be a liver-type fatty acid-binding protein standard having the coefficient of change in oxidation set to 1.4 or less, or may not be a liver-type fatty acid-binding protein standard having the coefficient of change in oxidation set to 1.4 or less; however, it is preferable that the liver-type fatty acid-binding protein standard according to the second aspect is a liver-type fatty acid-binding protein standard having the coefficient of change in oxidation set to 1.4 or less.

(Mutant Liver-Type Fatty Acid-Binding Protein)

The mutant liver-type fatty acid-binding protein according to the third aspect may be a protein that is used for the liver-type fatty acid-binding protein standard according to the first aspect, or may not be a protein that is used for the liver-type fatty acid-binding protein standard according to the first aspect, and it is preferable that the mutant liver-type fatty acid-binding protein comprises an amino acid sequence having at least 90% identity with SEQ ID NO:1 of the Sequence Listing and has one or more methionines at positions 19, 74, and 113 substituted by non-polar amino acids other than methionine. The mutant liver-type fatty acid-binding protein according to the third aspect can stabilize the binding capacity of a substance that specifically binds to liver-type fatty acid-binding protein (for example, an antibody), by having one or more methionines at positions 19, 74, and 113 substituted by non-polar amino acids other than methionine. In addition to methionine, oxidative modification of a disulfide bond or a cysteine residue that is subjected to direction addition of oxygen; a lysine residue, an arginine residue, and a proline residue, which are carbonylated; a tyrosine residue that is nitrified; and the like is known (Toda T., et al., Kiso Roka Kenkyu (Basic Studies on Aging), 35(3); 17-22, 2011); however, when the amino acids substituting one or more methionines at positions 19, 74, and 113 are non-polar amino acids, oxidative modification can be prevented.

SEQ ID NO:1 represents the amino acid sequence of wild type human L-FABP protein (hereinafter, also referred to L-FABP WT). The "amino acid sequence having at least 90% identity" as used in the present specification means that the identity of amino acids is 90% or higher, and the identity is preferably 95% or higher, and more preferably 97% or higher. Even for a mutant protein of the wild type human liver-type fatty acid-binding protein set forth in SEQ ID NO:1 of the Sequence Listing caused by substitution, insertion, deletion, addition, and the like on the amino acid sequence, as long as the mutation is mutation with high preservability for the three-dimensional structure of the wild type human liver-type fatty acid-binding protein, all of such mutant proteins can belong to the scope of liver-type fatty acid-binding protein. Specifically, even for a mutant protein having an identity of lower than 90% (for example, an identity of 85% or higher) with SEQ ID NO:1 of the Sequence Listing, which is obtained by adding one or a plurality of amino acids (for example, histidine (His) and alanine (Ala)) to at least one terminus selected from the group consisting of the N-terminus and the C-terminus of an amino acid sequence having at least 90% identity with SEQ ID NO:1 of the Sequence Listing, as long as the mutations are mutations with high preservability for the three-dimensional structure of the wild type human liver-type fatty acid-binding protein, all of such mutant proteins can belong to the scope of liver-type fatty acid-binding protein. The side chains of the amino acids that serve as constituent elements of a protein may respectively vary in terms of hydrophobicity, electric charge, size, and the like; however, several relations with high preservability in a sense that the overall three-dimensional structure (also referred to as steric structure) of a protein is substantially not affected, are known empirically or by physicochemical actual measurement. In regard to substitution of amino acid residues, examples include glycine (Gly) with proline (Pro), Gly with alanine (Ala) or valine (Val), leucine (Leu) with isoleucine (Ile), glutamic acid (Glu) with glutamine (Gln), aspartic acid (Asp) with asparagine (Asn), cysteine (Cys) with threonine (Thr), Thr with serine (Ser) or Ala, and lysine (Lys) with arginine (Arg).

There are no particular limitations on the method for obtaining the mutant liver-type fatty acid-binding protein, and the protein may be a protein synthesized by chemical synthesis, or may be a recombinant protein produced by a gene recombination technology. Since the amino acid sequence and gene sequence of L-FABP protein have already been reported (Veerkamp and Maatman, Prog. Lipid Res., 34:17-52, 1995), for example, the mutant liver-type fatty acid-binding protein can be produced by designing primers on the basis of those sequences, cloning cDNA from an appropriate cDNA library or the like by a PCR method, and performing gene recombination using this cDNA.

Regarding the mutant liver-type fatty acid-binding protein according to the third aspect, it is preferable that two or more methionines including methionine at positions 19, 74, and 113 are substituted by non-polar amino acids other than methionine; it is more preferable that two or more methionines including methionine at position 19 is substituted by a non-polar amino acid other than methionine; and it is even more preferable that all of methionines at positions 19, 74, and 113 are substituted by non-polar amino acids other than methionine.

Regarding the non-polar amino acids substituting one or more methionines at positions 19, 74, and 113, one or more methionines at positions 19, 74, and 113 may be substituted by identical non-polar amino acids, or may be substituted by different non-polar amino acids. The non-polar amino acids substituting one or more methionines at positions 19, 74, and 113 are preferably leucine, isoleucine, valine, alanine, phenylalanine, and tryptophan, and from the viewpoint of having a structure similar to that of methionine that does not significantly change the binding property of an antibody, the non-polar amino acids are more preferably leucine, isoleucine, valine, and alanine; even more preferably leucine, isoleucine, and valine; particularly preferably leucine and isoleucine; and most preferably leucine.

(DNA Encoding Mutant Liver-Type Fatty Acid-Binding Protein)

The DNA according to the fourth aspect is a DNA encoding the mutant liver-type fatty acid-binding protein. The DNA encoding the mutant liver-type fatty acid-binding protein (mutant gene) can be produced by any arbitrary method such as chemical synthesis, a genetic engineering technique, or mutagenesis. As explained above, since the amino acid sequence and gene sequence of L-FABP protein have already been reported, for example, the DNA can be obtained by designing primers on the basis of those sequences, cloning cDNA from an appropriate cDNA library or the like by a PCR method, and performing gene recombination using this cDNA. A site-specific mutagenesis method, which is one of genetic engineering methods, is useful because it is a technique by which a particular mutation can be introduced into a particular position, and the site-specific mutagenesis method can be carried out according to the methods described in Molecular Cloning, $2^{nd}$ Edition, Current Protocols in Molecular Biology, and the like.

(Transformed Cell)

The cell according to the fifth aspect is a cell that has been transformed with the DNA according to the fourth aspect. A transformed cell can be produced by introducing the DNA according to the fourth aspect or a recombinant vector containing the DNA according to the fourth aspect into an appropriate host. A recombinant vector containing the DNA can be produced by a general gene recombination technology using an appropriate host-vector system. Regarding an appropriate vector, *Escherichia coli*-derived plasmids (for example, pBR322, pUC118, and others), *Bacillus subtilis*-derived plasmids (for example, pUB110, pSH19, and others), and animal viruses such as bacteriophages, retroviruses, and vaccinia viruses can be utilized. Examples of the host cell into which the DNA or a recombinant vector containing the DNA is introduced include bacteria and yeast. Examples of bacterial cells include Gram-positive bacteria such as bacteria of the genus *Corynebacterium* (for example, *Corynebacterium glutamicum*), bacteria of the genus *Bacillus* (for example, *Bacillus subtilis*), and bacteria of the genus *Streptomyces*; and Gram-negative bacteria such as *Escherichia coli*. Transformation of these bacteria may be carried out by a protoplast method, or by a known method using competent cells. Examples of yeast cells include cells belonging to *Saccharomyces* or *Schizosaccharomyces*, and for example, *Saccharomyces cerevislae* and *Saccharomyces kluyveri* may be used. Examples of the method for introducing a recombinant vector into a yeast host include an electroporation method, a spheroblast method, and a lithium acetate method. Regarding the cell transformed with the DNA, from the viewpoint that the mutant liver-type fatty acid-binding protein is produced efficiently and the purification of liver-type fatty acid-binding protein that will be described below does not need complicated processes, a protein secretion and expression system using *Corynebac*- terium glutamicum (CORYNEX (registered trademark); manufactured by Ajinomoto Co., Inc.) is preferred.

(Method of Producing Mutant Liver-Type Fatty Acid-Binding Protein Described Above)

The method of producing the mutant liver-type fatty acid-binding protein according to the sixth aspect preferably includes a step of culturing the transformed cell and collecting the above-mentioned protein. The transformed cell is cultured in an adequate nutrient medium under the conditions enabling expression of the introduced gene. In order to collect the protein from a culture product of the transformed cell, conventional isolation and purification methods of protein may be used. For example, when the protein is expressed in a state of being dissolved in cells, after completion of culture, the cells are collected by centrifugation and suspended in a water-based buffer solution, subsequently the cells are disrupted using an ultrasonic disruptor, and a cell-free extract is obtained. From a supernatant obtained by centrifuging the cell-free extract, a purified standard can be obtained by using conventional protein isolation and purification methods, namely, techniques including a solvent extraction method, a salting-out method using ammonium sulfate or the like, a desalting method, a precipitation method using an organic solvent, an anion exchange chromatography method using a resin such as diethylaminoethyl (DEAE) sepharose, a cation exchange chromatography method using a resin such as S-Sepharose FF (manufactured by Pharmacia LLC), a hydrophobic chromatography method using a resin such as butyl sepharose or phenyl sepharose, a gel filtration method using a molecular sieve, an affinity chromatography method, a chromatofocusing method, an electrophoresis method such as isoelectric point electrophoresis, singly or in combination. When a protein excretion expression system (CORYNEX (registered trademark): manufactured by Ajinomoto Co., Inc.) that uses Corynebacterium glutamicum is used, a complicated process of disrupting cells and obtaining a cell-free extract is not needed, and a purified standard can be obtained by purification by anion exchange chromatography (for example, HiTrapQ FF5 mL FPLC column) after optional centrifugation, or the like.

(Liver-Type Fatty Acid-Binding Protein Standard According to Seventh Aspect)

Figure 6A:
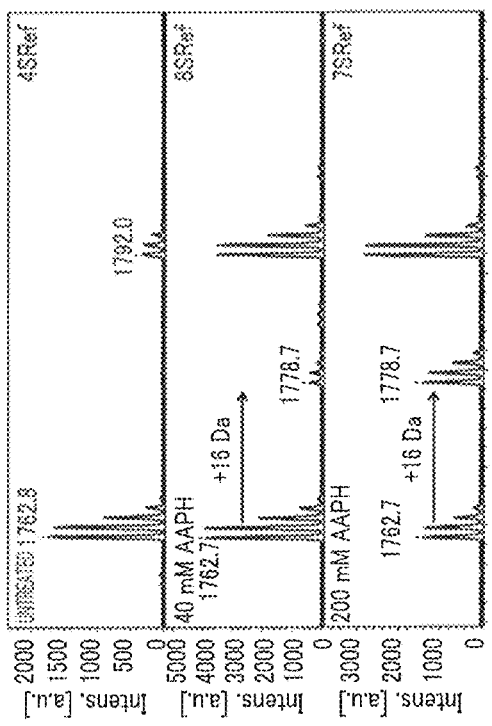
FIG. 6(a) is a diagram showing the MS spectra of peptide fragment No. 1 including Met1, which was obtained by trypsin digestion of human L-FABP protein after the reaction with AAPH at the various concentrations (40 mM and 200 mM)
Figure 6C:
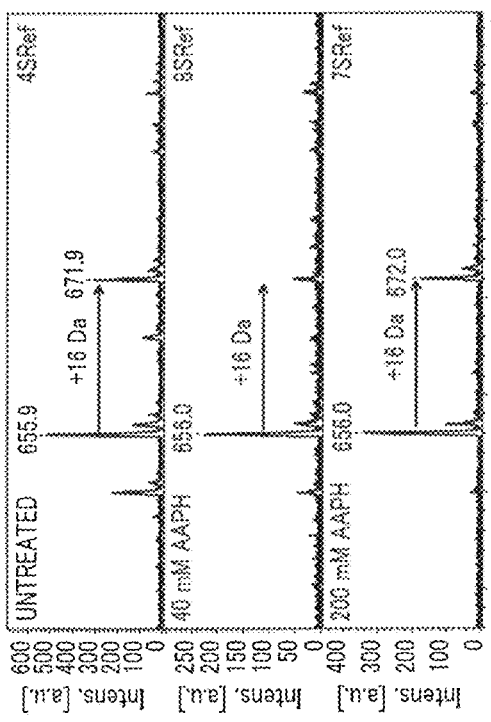
FIG. 6(c) is a diagram showing MS spectra of peptide fragment No. 9 including Met74 and peptide fragment No. 10, which were obtained by trypsin digestion of human L-FABP protein after the reaction with AAPH at the various concentrations.
Figure 6B:
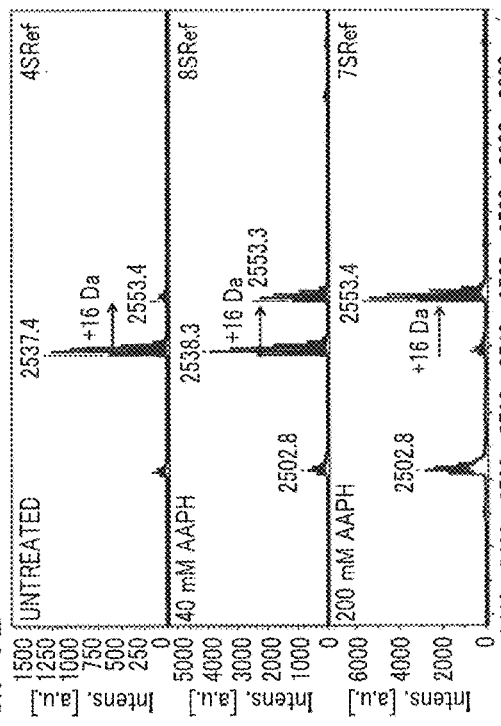
FIG. 6(b) is a diagram showing MS spectra of peptide fragment No. 2 including Met19, which was obtained by trypsin digestion of human L-FABP protein after the reaction with AAPH at the various concentrations.
Figure 6D:
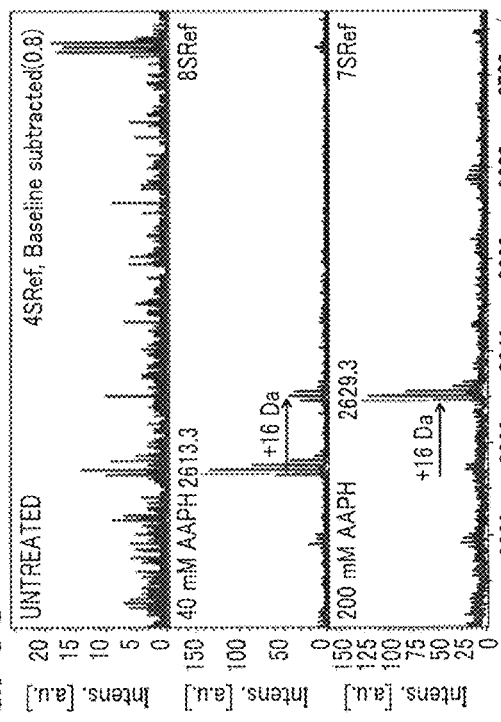
FIG. 6(d) is a diagram showing MS spectra of peptide fragment No. 14 including Met113 and peptide fragment No. 15, which were obtained by trypsin digestion of human L-FABP protein after the reaction with AAPH at the various concentrations.

The liver-type fatty acid-binding protein standard according to the seventh aspect includes a liver-type fatty acid-binding protein comprising an amino acid sequence having at least 90% identity with SEQ ID NO:1 of the Sequence Listing, in which the oxidation ratio of methionine at position 19 is 30% or higher, or the oxidation ratio of methionine at position 113 is 70% or higher. As will be described below with reference to FIG. 13, when the oxidation ratio of methionine at position 19 is 30% or higher, or the oxidation ratio of methionine at position 113 is 70% or higher, an increase in the oxidation ratio is further regulated, and as a result, the variation in the binding capacity caused by a specifically binding substance can be regulated. The liver-type fatty acid-binding protein standard according to the seventh aspect may be a liver-type fatty acid-binding protein standard having the coefficient of change in oxidation set to 1.4 or less, or may not be a liver-type fatty acid-binding protein standard having the coefficient of change in oxidation set to 1.4 or less; however, it is preferable that the protein standard is a liver-type fatty acid-binding protein standard having the coefficient of change in oxidation set to 1.4 or less. In regard to the liver-type fatty acid-binding protein standard according to the seventh aspect, in a case in which the oxidation ratio of methionine at position 19 is adjusted to be 30% or higher, from the viewpoint that the variation in the binding capacity caused by a specifically binding substance can be further regulated, it is acceptable that at least one methionine selected from the group consisting of methionines at positions 74 and 113 is not substituted by the above-mentioned non-polar amino acids other than methionine. From a similar viewpoint, in a case in which the oxidation ratio of methionine at position 113 is adjusted to be 70% or higher, it is acceptable that at least one methionine selected from the group consisting of methionines at positions 19 and 74 is not substituted by the above-mentioned non-polar amino acids other than methionine. Furthermore, the oxidation ratio of methionine at position 19 is preferably 35% or higher, more preferably 38% or higher, even more preferably 40% or higher, and particularly preferably 45% or higher, from the viewpoint that the variation in the binding capacity caused by a specifically binding substance can be further suppressed. From a similar viewpoint, the oxidation ratio of methionine at position 113 is preferably 73% or higher, more preferably 75% or higher, and even more preferably 80% or higher. Regarding the method for measuring the oxidation ratio, for example, the oxidation ratio can be calculated from a comparison between the peak in the case of a non-oxidation treated sample and the peak in the case of an oxidation-treated sample in the MS spectra of peptide fragments containing Met19 in FIG. 6(b) that will be described below, the MS spectra of peptide fragments containing Met74 in FIG. 6(c), and the MS spectra of peptide fragments containing Met113 in FIG. 6(d). Furthermore, the liver-type fatty acid-binding protein standard may also be such that the oxidation ratio of methionine at position 74 is 60% or higher, without depending on the oxidation ratio of methionine at position 19 and the oxidation ratio of methionine at position 113, from the viewpoint that the variation in the binding capacity caused by a specifically binding substance can be regulated. In this case, it is preferable that the oxidation ratio of methionine at position 74 is 65% or higher; it is more preferable that the oxidation ratio of methionine at position 74 is 70% or higher; it is even more preferable that the oxidation ratio of methionine at position 74 is 75% or higher; it is particularly preferable that the oxidation ratio of methionine at position 74 is 80% or higher; and it is most preferable that the oxidation ratio of methionine at position 74 is 85% or higher. A liver-type fatty acid-binding protein standard having the above-described oxidation ratio can be produced using an oxidant such as AAPH and can also be produced by air oxidation.

(Liver-Type Fatty Acid-Binding Protein Standard According to Eighth Aspect)

The liver-type fatty acid-binding protein standard according to the eighth aspect is a liver-type fatty acid-binding protein standard including at least one fatty acid selected from the group consisting of arachidonic acid, oleic acid, 8-iso-prostaglandin $F_{2\alpha}$, and 2,3-dinor-8-iso-prostaglandin $F_{2\alpha}$ in an amount such that the coefficient of change in oxidation becomes 1.4 or less, and also including a liver-type fatty acid-binding protein comprising an amino acid sequence having at least 90% identity with SEQ ID NO:1 of the Sequence Listing. It is preferable that the amount such that the coefficient of change in oxidation becomes 1.4 or less is an amount including the amount of the fatty acid in a molar amount 30 times or more the molar amount of the liver-type fatty acid-binding protein. The liver-type fatty acid-binding protein standard according to the eighth aspect may be a liver-type fatty acid-binding protein standard having the coefficient of change in oxidation set to 1.4 or less, or may not be a liver-type fatty acid-binding protein standard having the coefficient of change in oxidation set to 1.4 or less; however, it is preferable that the liver-type fatty acid-binding protein standard is a liver-type fatty acid-binding protein standard having the coefficient of change in oxidation set to 1.4 or less.

As will be described below with reference to FIG. 15, the inventors of the present invention found that the antibody binding capacity of L-FABP protein changes depending on the type (FIG. 15(b)) or concentration of the fatty acid that binds to L-FABP protein. As the liver-type fatty acid-binding protein standard according to the eighth aspect includes at least one fatty acid selected from the group consisting of arachidonic acid, oleic acid, 8-iso-prostaglandin $F_{2\alpha}$, and 2,3-dinor-8-iso-prostaglandin $F_{2\alpha}$ in an amount such that the coefficient of change in oxidation becomes 1.4 or less (preferably, a molar amount, as the total content in a case in which there are a plurality of fatty acids, 30 times or more the molar amount of the liver-type fatty acid-binding protein), when L-FABP protein that constitutes the standard is expressed, or in an assay system used as a standard, even if the type of the binding fatty acid (for example, arachidonic acid, oleic acid, 8-iso-prostaglandin $F_{2\alpha}$, or 2,3-dinor-8-iso-prostaglandin $F_{2\alpha}$), the binding amount, and the degree of peroxidation vary depending on the expression system or the site or organ of expression based on biological species of different origins, the variation in the binding capacity caused by a specifically binding substance is regulated, and the liver-type fatty acid-binding protein standard can function as a standard material for measurement, a substance for accuracy management, or the like. From the viewpoint that the variation in the binding capacity caused by a specifically binding substance is further regulated, it is preferable that at least one fatty acid selected from the group consisting of arachidonic acid, oleic acid, 8-iso-prostaglandin $F_{2\alpha}$, and 2,3-dinor-8-iso-prostaglandin $F_{2\alpha}$ is included in a molar amount 50 times or more, as the total content in a case in which there are a plurality of fatty acids, more preferably in a molar amount 75 times or more, even more preferably in a molar amount 100 times or more, and particularly preferably in a molar amount 300 times or more, relative to the molar amount of the liver-type fatty acid-binding protein.

More particularly, when the fatty acid is arachidonic acid, it is preferable that the fatty acid is included in a molar amount 30 times or more, more preferably in a molar amount 50 times or more, even more preferably in a molar amount 75 times or more, and particularly preferably in a molar amount 100 times or more, relative to the molar amount of the liver-type fatty acid-binding protein. Furthermore, when the fatty acid is oleic acid, it is preferable that the fatty acid is included in a molar amount 100 times or more, more preferably in a molar amount 300 times or more, and even more preferably in a molar amount 1,000 times or more, relative to the molar amount of the liver-type fatty acid-binding protein. When the fatty acid is 8-iso-prostaglandin $F_{2\alpha}$, it is preferable that the fatty acid is included in a molar amount 500 times or more, and more preferably in a molar amount 1,000 times or more, relative to the molar amount of the liver-type fatty acid-binding protein.

In a case in which the liver-type fatty acid-binding protein standard according to the eighth aspect includes bovine serum albumin (BSA) as an adsorption preventing agent, from the viewpoint that the fatty acid adsorbs to BSA, it is preferable that the protein standard includes at least one fatty acid selected from the group consisting of arachidonic acid, oleic acid, 8-iso-prostaglandin $F_{2\alpha}$, and 2,3-dinor-8-iso-prostaglandin $F_{2\alpha}$ in a molar amount 0.02 to 10 times, and more preferably in a molar amount 0.2 to 5 times, as the total content in a case in which there are a plurality of fatty acids, relative to the molar amount of BSA. In a case in which the fatty acid is arachidonic acid when the standard includes BSA, it is preferable that arachidonic acid is included in a molar amount 1,000 times or more, more preferably in a molar amount 10,000 times or more, even more preferably in a molar amount 100,000 times or more, and particularly preferably in a molar amount 200,000 times or more, relative to the molar amount of the liver-type fatty acid-binding protein. In a case in which the fatty acid is oleic acid when the standard includes BSA, it is preferable that oleic acid is included in a molar amount 100,000 times or more, and more preferably in a molar amount 200,000 times or more, relative to the molar amount of the liver-type fatty acid-binding protein. In a case in which the fatty acid is 8-iso-prostaglandin $F_{2\alpha}$ when the standard includes BSA, it is preferable that 8-iso-prostaglandin $F_{2\alpha}$ is included in a molar amount 200,000 times or more the molar amount of the liver-type fatty acid-binding protein. The liver-type fatty acid-binding protein standard according to the eighth aspect including a particular amount of at least one fatty acid can be produced by adding the at least one fatty acid in a molar amount, as the total content in a case in which there are a plurality of fatty acids, 30 times or more the molar amount of the liver-type fatty acid-binding protein to a liquid containing the liver-type fatty acid-binding protein standard, or under the conditions of cell culture and protein isolation or purification resulting in such a content. The content of the at least one fatty acid corresponds to the amount of addition. The upper limit of the content of the fatty acid is not particularly limited; however, when the adsorption preventing agent described below is further incorporated, since the fatty acid may adsorb to the adsorption preventing agent, the fatty acid can be incorporated in a 500,000 times molar amount, preferably in a molar amount 300,000 times or less, more preferably in a molar amount 200,000 times or less, and even more preferably in a molar amount 10,000 times or less, the molar amount of the liver-type fatty acid-binding protein.

In regard to the liver-type fatty acid-binding protein standard according to any one of the first, second, seventh, and eighth aspects, the variation range (for example, variation range caused by oxidation) obtained before and after two weeks at 37° C. of a measured value for a measurement using a substance specifically binding to liver-type fatty acid-binding protein is not particularly limited as long as the effects of the present invention are not impaired; however, the variation range is preferably 15% or less, more preferably 10% or less, even more preferably 5% or less, and particularly preferably 1% or less. The liver-type fatty acid-binding protein standard according to any one of the first, second, seventh, and eighth aspects may include, as necessary, an adsorption preventing agent, any arbitrary buffer solution, any arbitrary surfactant, and the like. The adsorption preventing agent is not particularly limited as long as the effects of the present invention are not impaired; however, examples include BSA, casein, skimmed milk, and polyethylene glycol, while the adsorption preventing agent is preferably BSA. The content of the adsorption preventing agent in the liver-type fatty acid-binding protein standard according to any one of the first, second, seventh, and eighth aspects is not particularly limited as long as the effects of the present invention are not impaired; however, the content of the adsorption preventing agent is preferably 0.05% to 10% by mass.

The liver-type fatty acid-binding protein standard according to any one of the first, second, seventh, and eighth aspects is preferably a liver-type fatty acid-binding protein standard that is supplied to sales, from the viewpoint of being utilized for practical use and commercial use. The liver-type fatty acid-binding protein standard that is supplied to sales is not a protein that has been sold, specifically a liver-type fatty acid-binding protein standard that has been left for a long time period after being sold. The liver-type fatty acid-binding protein standard according to any one of the first, second, seventh, and eighth aspects is useful as a standard substance for measurement or a substance for accuracy management of a kit for measuring liver-type fatty acid-binding protein in a sample by an immunological technique utilizing an antigen-antibody reaction, and it is preferable that the liver-type fatty acid-binding protein standard is used as a standard substance (preparation) for a measurement such as detection or quantification of L-FABP protein utilizing specific binding by an anti-L-FABP protein antibody that specifically binds to L-FABP protein. Examples of the measurement such as detection or quantification of L-FABP protein where the liver-type fatty acid-binding protein standard according to any one of the first, second, seventh, and eighth aspects is used, include assays employing enzyme immunoassay (EIA, ELISA), fluorescent enzyme immunoassay (FLEIA), chemiluminescent enzyme immunoassay (CLEIA), chemiluminescent immunoassay (CLIA), electrochemical luminescent immunoassay (ECLIA), immunochromatographic assay (ICA), a latex aggregation method (LA), a fluorescent antibody method (FA), radioimmunoassay (RIA), Western blotting method (WB), and an immunoblotting method. The measurement is preferably an assay employing a sandwich ELISA method of using two kinds of antibodies having different recognition sites for an antigen (L-FABP protein) in combination. Regarding the two kinds of antibodies having different recognition sites, it is preferable that one of the antibodies is used as a solidified antibody bound to the surface in the wells of a microplate, while the other is used as a labeled antibody for detection or quantification. There are no particular limitations on the label for the labeled antibody, and examples include an enzyme label such as a peroxidase label, a fluorescent label, an ultraviolet label, and a radiation label.

Examples of antibodies having different recognition sites for an antigen (L-FABP protein) include antibodies including antibodies selected from the group consisting of anti-L-FABP antibody clone 1, clone 2, clone L, and clone F. A combination including anti-L-FABP antibody clone L or a combination including anti-L-FABP antibody clone 2 is preferred; a combination including anti-L-FABP antibody clone L is more preferred; it is even more preferable that anti-L-FABP antibody clone L is used as a solidified antibody, while an arbitrary anti-L-FABP antibody is used as a labeled antibody; and it is particularly preferable that anti-L-FABP antibody clone L is used as a solidified antibody, while anti-L-FABP antibody clone 2 is used as a labeled antibody.

Regarding an L-FABP protein measurement kit used for such an assay, a kit including the liver-type fatty acid-binding protein standard according to any one of the first, second, seventh, and eighth aspects as a standard and including the anti-L-FABP protein antibody as a reagent; it is more preferable that the kit further includes a labeled anti-L-FABP protein antibody; and the kit may also include, if necessary, an adsorption preventing agent (BSA or the like), a pretreatment liquid (any arbitrary buffer solution, any arbitrary surfactant, or the like), a reaction buffer solution (any arbitrary buffer solution, or the like), a chromogenic substrate (3,3',5,5'-tetramethylbenzidine, aqueous hydrogen peroxide, or the like), and the like. The L-FABP protein measurement kit is preferably a kit using a sandwich ELISA method of using two kinds of antibodies having different recognition sites for an antigen in combination, and is more preferably a kit using any arbitrary anti-L-FABP antibody for the solid phase and anti-L-FABP antibody clone 2 as a labeled antibody. Examples of a specific embodiment of the L-FABP protein measurement kit using a sandwich ELISA method include kits of the following (1) to (9):

(1) L-FABP antibody-coated microplate . . . anti-human L-FABP mouse monoclonal antibody-immobilized well
(2) Pretreatment solution
(3) Assay buffer
(4) The 2nd Ab-POD Conjugate . . . Anti-human L-FABP mouse monoclonal antibody conjugated to peroxidase [derived from a clone 2-producing cell strain]
(5) Substrate solution
(6) Wash agent (any arbitrary buffer solution, surfactant, or the like)
(7) Stop solution (1 N sulfuric acid or the like)
(8) Standard diluent (any arbitrary buffer solution or the like)
(9) Liver-type fatty acid-binding protein standard As the (9) liver-type fatty acid-binding protein standard, a liquid obtained by mixing any arbitrary buffer solution with recombinant human L-FABP has been conventionally used; however, a liquid obtained by mixing any arbitrary buffer solution with the liver-type fatty acid-binding protein standard described above is preferred. The concentration of the standard is not particularly limited, and for example, the concentration may be 10 to 10,000 ng/mL, preferably 50 to 5,000 ng/mL, more preferably 100 to 1,000 ng/mL, even more preferably 200 to 800 ng/mL, and particularly preferably 300 to 600 ng/mL. A commercially available product of a kit similar to the L-FABP protein measurement kit utilizing a sandwich ELISA method of using the liver-type fatty acid-binding protein standard according to any one of the first, second, seventh, and eighth aspects, except that conventional recombinant human L-FABP is used as the liver-type fatty acid-binding protein standard, may be "RENAPRO L-FABP TEST TMB" (manufactured by CMIC HOLDINGS Co., Ltd.).

A preservative solution for a liver-type fatty acid-binding protein standard comprising L-FABP protein is preferably prepared as a protein preservative buffer solution containing BSA, for the purpose of preventing protein adsorption. For example, the following protein preservative buffer solution may be used.

(Protein Preservative Buffer Solution)
10 mM phosphate buffer (pH 7.2), 150 mM NaCl, 1.0% BSA, and 0.1% $NaN_3$ <Method for Evaluating Liver-Type Fatty Acid-Binding Protein Standard by Using Coefficient of Change in Oxidation as Index>

The method of evaluating a liver-type fatty acid-binding protein standard according to the ninth aspect evaluates the difficulties in oxidation variation of the above-described standard by using the coefficient of change in oxidation as an index, the coefficient of change in oxidation being represented as the ratio of a measured value obtained after an oxidation treatment with respect to the measured value obtained using the liver-type fatty acid-binding protein standard before the oxidation treatment. In regard to the method of evaluating a liver-type fatty acid-binding protein standard according to the ninth aspect, from the viewpoint of regulating the oxidation variation range, it is preferable that the coefficient of change in oxidation is 1.4 or less, and more preferably 1.3 or less. The lower limit of the coefficient of change in oxidation is not particularly limited as long as the effects of the present invention are not impaired; however, for example, the lower limit may be 0.8 or higher, preferably 0.9 or higher, and more preferably 1.0 or higher.

<Method of Regulating Variation Range of Measured Value in Measurement Using Liver-Type Fatty Acid-Binding Protein Standard>

The method of regulating the variation range of a measured value attributed to liver-type fatty acid-binding protein in a measurement using the liver-type fatty acid-binding protein standard according to the tenth aspect includes at least any one selected from the group consisting of the following:

(1) substituting one or more methionines at positions 19, 74, and 113 of a liver-type fatty acid-binding protein comprising an amino acid sequence having at least 90% identity with SEQ ID NO:1 of the Sequence Listing, with non-polar amino acids other than methionine, and substituting at least methionine at position 19 with a non-polar amino acid other than methionine;

(2) adjusting the oxidation ratio of methionine at position 19 of a liver-type fatty acid-binding protein comprising an amino acid sequence having at least 90% identity with SEQ ID NO:1 of the Sequence Listing to be 30% or higher, or adjusting the oxidation ratio of methionine at position 113 to be 70% or higher; and (3) incorporating at least one fatty acid selected from the group consisting of arachidonic acid, oleic acid, 8-iso-prostaglandin $F_{2\alpha}$, and 2,3-dinor-8-iso-prostaglandin $F_{2\alpha}$ into the liver-type fatty acid-binding protein standard. In regard to the method according to the tenth aspect, the oxidation ratio of methionine at position 19 is preferably 35% or higher, more preferably 38% or higher, even more preferably 40% or higher, and particularly preferably 45% or higher. Furthermore, the oxidation ratio of methionine at position 113 is preferably 73% or higher, more preferably 75% or higher, and even more preferably 80% or higher. In regard to the method according to the tenth aspect, the content of the at least one fatty acid incorporated into the liver-type fatty acid-binding protein standard is not particularly limited as long as the effects of the present invention are not impaired; however, the content is preferably a molar amount 30 times or more, more preferably a molar amount 50 times or more, even more preferably a molar amount 75 times or more, particularly preferably a molar amount 100 times or more, and particularly preferably a molar amount 300 times or more, relative to the molar amount of the liver-type fatty acid-binding protein. The upper limit of the content of the fatty acid is not particularly limited; however, in a case in which the adsorption preventing agent is further incorporated, the fatty acid may adsorb to the adsorption preventing agent. Therefore, the fatty acid can be incorporated in a 500,000-fold molar amount, preferably in a molar amount 200,000 times or less, more preferably in a molar amount 100,000 times or less, even more preferably in a molar amount 10,000 times or less, and particularly preferably in a molar amount 1,000 times or less, relative to the molar amount of the liver-type fatty acid-binding protein. When the method according to the tenth aspect is used, the variation range of a measured value in a measurement using a substance specifically binding to liver-type fatty acid-binding protein can be regulated, and preferably, the variation range before and after two weeks at 37° C. can be adjusted to be 15% or less; more preferably, the variation range can be adjusted to be 10% or less; even more preferably, the variation range can be adjusted to be 5% or less; and particularly preferably, the variation range can be adjusted to be 1% or less.

<Method of Drawing Calibration Curve and Method for Quantifying Liver-Type Fatty Acid-Binding Protein>

The method of drawing a calibration curve for a liver-type fatty acid-binding protein according to the eleventh aspect uses the liver-type fatty acid-binding protein standard according to any one of the first, second, seventh, and eighth aspects. Specifically, a calibration curve can be drawn based on the relation between the intensity of a label (for example, enzyme label intensity, fluorescence intensity, ultraviolet intensity, or radiation intensity) and the amount of the standard (for example, concentration). The method of quantifying a liver-type fatty acid-binding protein in a sample according to the twelfth aspect uses a calibration curve drawn by the method according to the eleventh aspect. Specifically, the label intensity of a liver-type fatty acid-binding protein in a sample labeled with a labeled antibody or the like is measured under conditions similar to those for drawing a calibration curve as described above, and the liver-type fatty acid-binding protein in the sample can be detected or quantified based on the calibration curve (for example, comparison).

EXAMPLES

Hereinafter, the present invention will be described in more detail by way of Examples; however, the scope of the present invention is not intended to be limited to these Examples.

Reference Example (Structural Change in L-FABP Protein by Oxidation)

Figures 2A, 2B:
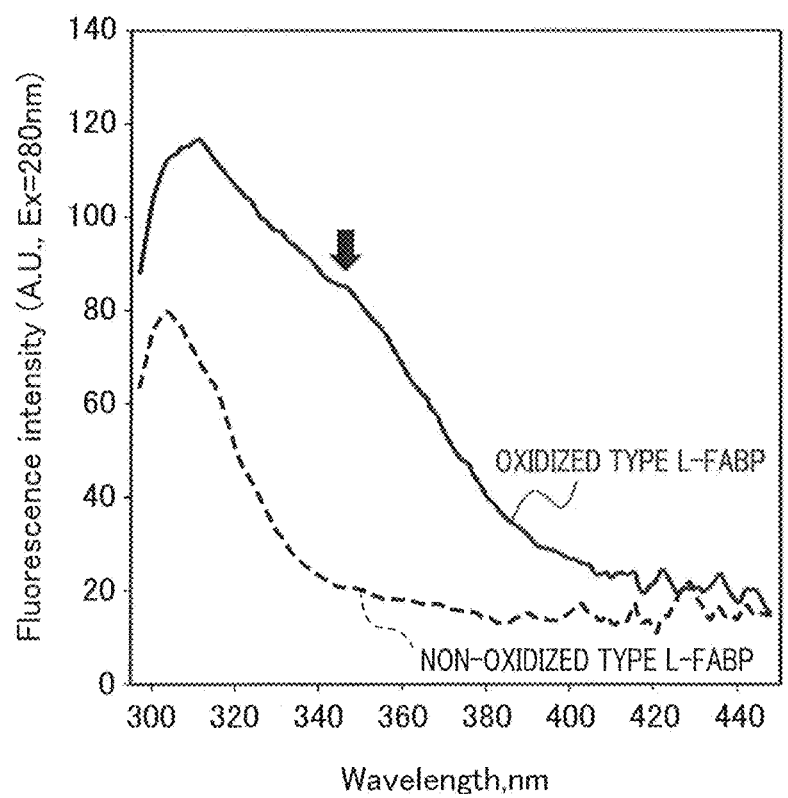
FIG. 2(a) is a diagram showing the molecular weight measurement results for oxidized type L-FABP and non-oxidized type L-FABP by LC-ESI-MS.
FIG. 2(b) is a diagram showing the fluorescence spectra of oxidized type L-FABP and non-oxidized type L-FABP.

L-FABP protein was treated with AAPH. The results are presented in FIG. 2(a) and FIG. 2(b). FIG. 2(a) is a diagram showing the molecular weight measurement results made by LC-ESI-MS for oxidized type L-FABP and non-oxidized type L-FABP, and FIG. 2(b) is a diagram showing fluorescence spectra of oxidized type L-FABP and non-oxidized type L-FABP. As is obvious from FIG. 2(a), an increase in the molecular weight corresponding to approximately two to three oxygen molecules from the theoretical molecular weight was observed in the oxidized type L-FABP. As is shown in FIG. 2(b), a fluorescence peak appears at near 350 nm (indicated by an arrow in the diagram) in the oxidized type L-FABP, and this means that the periphery of aromatic amino acids existing in the L-FABP protein has changed to a highly polar environment. Thus, it is thought that structural changes have occurred in the oxidized type L-FABP and the non-oxidized type L-FABP.

(Changes in ELISA Measured Value Caused by Oxidation)

Figure 3:
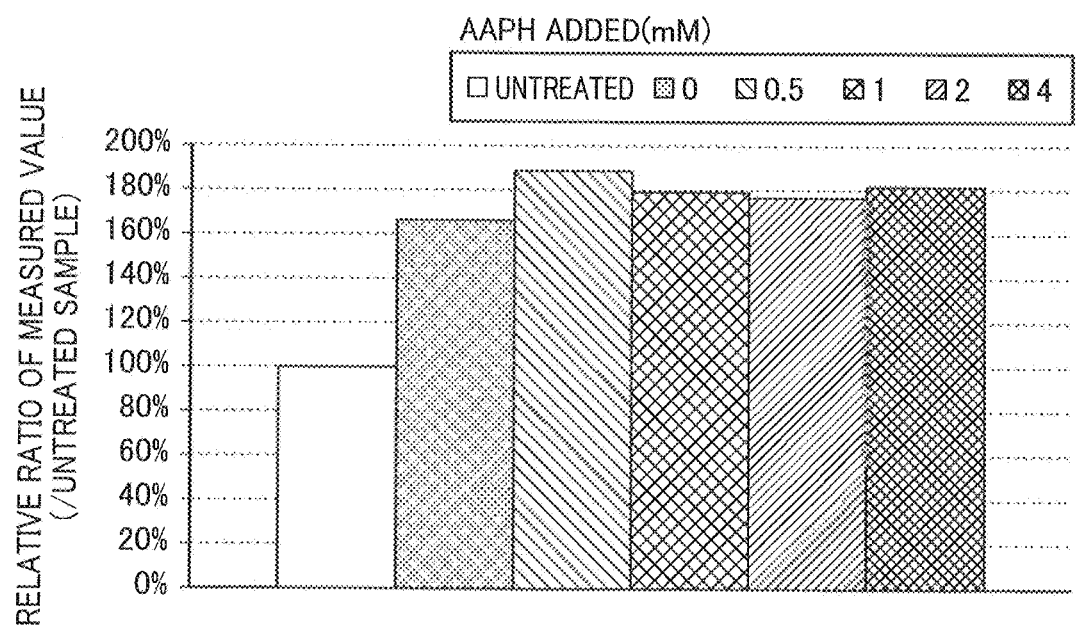
FIG. 3 is a diagram showing the changes in the ELISA measured value for L-FABP protein caused by AAPH treatment (proportions (%) obtainable by designating the measured value obtained without treatment as 100).

AAPH was added to an L-FABP protein solution so as to obtain a predetermined concentration, the mixture was allowed to react for one hour at room temperature, and an ELISA measurement was carried out. The results are presented in FIG. 3. It can be seen from FIG. 3 that the changes in the ELISA measured value caused by an AAPH treatment of L-FABP protein (proportions (%) obtainable by designating the measured value obtained without treatment as 100) have occurred. Furthermore, surprisingly, as shown in FIG. 3, even in the case of an non-AAPH-added sample ($H_2O$ was added), the ELISA measured value increased as a result of performing the reaction for one hour at room temperature, and it is thought that influence caused by air oxidation has occurred.

(Oxidation of Human L-FABP Protein)

Figure 4:
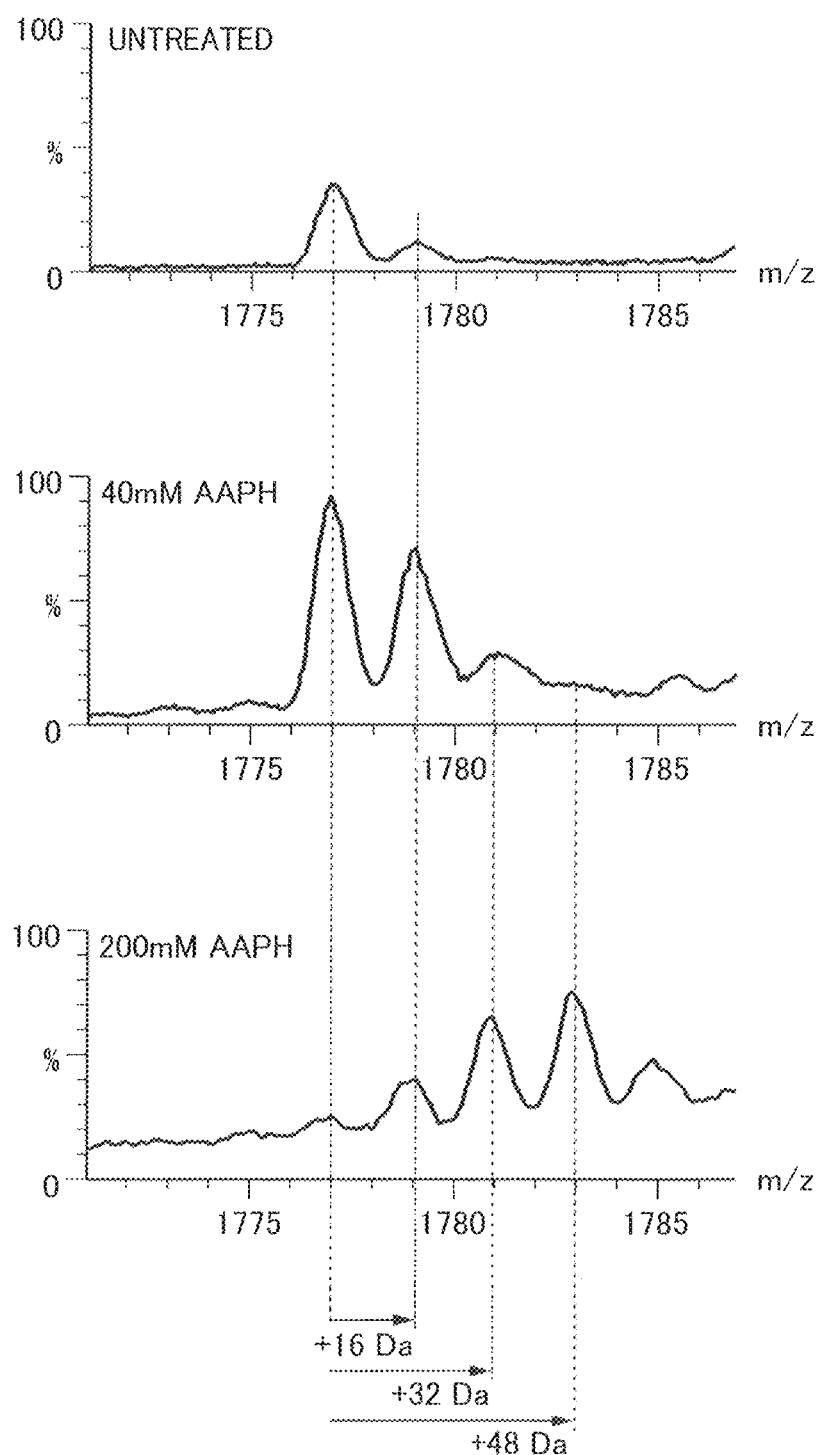
FIG. 4 is a diagram showing MS spectra obtained after adding AAPH at various concentrations to human L-FABP protein and causing the mixture to react for 1.5 hours at 37° C.

AAPH was added to human L-FABP protein at various concentrations (40 mM and 200 mM), and the mixtures were caused to react for 1.5 hours at 37° C. The results are shown in FIG. 4. FIG. 4 is a diagram showing MS spectra obtained after adding AAPH to human L-FABP protein at various concentrations (40 mM and 200 mM) and reacting the mixtures for 1.5 hours at 37° C. As shown in FIG. 4, increases in the molecular weight corresponding to one to three oxygen molecules were observed in L-FABP caused by an AAPH treatment.

(Oxidation of Methionine Contained in Human L-FABP Protein)

FIG. 5(*a*) is a diagram showing the amino acid sequence of human L-FABP protein set forth in SEQ ID NO:1, and FIG. 5(*b*) is a diagram showing suspected molecular weights of various peptide fragments that can produced by trypsin digestion of human L-FABP protein. The MS spectra of various peptide fragments obtained by digesting human L-FABP protein with trypsin after reacting the human L-FABP protein with AAPH at the above-described various concentrations (40 mM and 200 mM) were measured. FIG. 6(*a*) is a diagram showing MS spectra of peptide fragment No. 1 containing Met1 obtained by digesting human L-FABP protein with trypsin after reacting the human L-FABP protein with AAPH at the above-described various concentrations (40 mM and 200 mM); FIG. 6(*b*) is a diagram showing MS spectra of peptide fragment No. 2 containing Met19 obtained by trypsin digestion of human L-FABP protein after the reaction with AAPH at the above-described various concentrations; FIG. 6(*c*) is a diagram showing MS spectra of peptide fragment No. 9 and peptide fragment No. 10 containing Met74 obtained by trypsin digestion of human L-FABP protein after the reaction with AAPH at the above-described various concentrations; and FIG. 6(*d*) is a diagram showing MS spectra of peptide fragment No. 14 and peptide fragment No. 15 containing Met113 obtained by trypsin digestion of human L-FABP protein after the reaction with AAPH at the above-described various concentrations. It was found from the results shown in FIG. 6(*a*) to FIG. 6(*d*) that the sites of oxidative modification were methionine residues at positions 19, 74, and 113 (hereinafter, respectively referred to as Met19, Met74, and Met113).

Example 1

(Method of Producing Mutant L-FABP Protein)

A mutant protein having Met19 mutated with a leucine residue (hereinafter, also referred to as L-FABP M19L), a mutant protein having Met74 mutated with a leucine residue (hereinafter, also referred to as L-FABP M74L), a mutant protein having Met113 mutated with a leucine residue (hereinafter, also referred to as L-FABP M113L), a mutant protein having Met19 and Met74 respectively mutated with a leucine residue (hereinafter, also referred to as L-FABP M19L/M74L), a mutant protein having Met19 and Met113 respectively mutated with a leucine residue (hereinafter, also referred to as L-FABP M19L/M113L), a mutant protein having Met74 and Met113 respectively mutated with a leucine residue (hereinafter, also referred to as L-FABP M74L/M113L), and a mutant protein having three methionine residues (Met19, Met74, and Met113) respectively mutated with a leucine residue (hereinafter, also referred to as L-FABP M19L/M74L/M113L) were produced.

L-FABP M19L,
L-FABP M74L,
L-FABP M113L,
L-FABP M19L/M74L,
L-FABP M19L/M113L,
L-FABP M74L/M113L, and
L-FABP M19L/M74L/M113L were respectively expressed by utilizing a protein secretion and expression system (CORYNEX (registered trademark); manufactured by Ajinomoto Co., Inc.) using a Gram-positive bacterium, *Corynebacterium glutamicum*. The amino acid sequence of L-FABP M19L/M74L/M113L is set forth in SEQ ID NO:2 of the Sequence Listing described below. The gene sequence of L-FABP M19L/M74L/M113L used in the protein expression is set forth in SEQ ID NO:3 of the following Sequence Listing.

Figure 7:
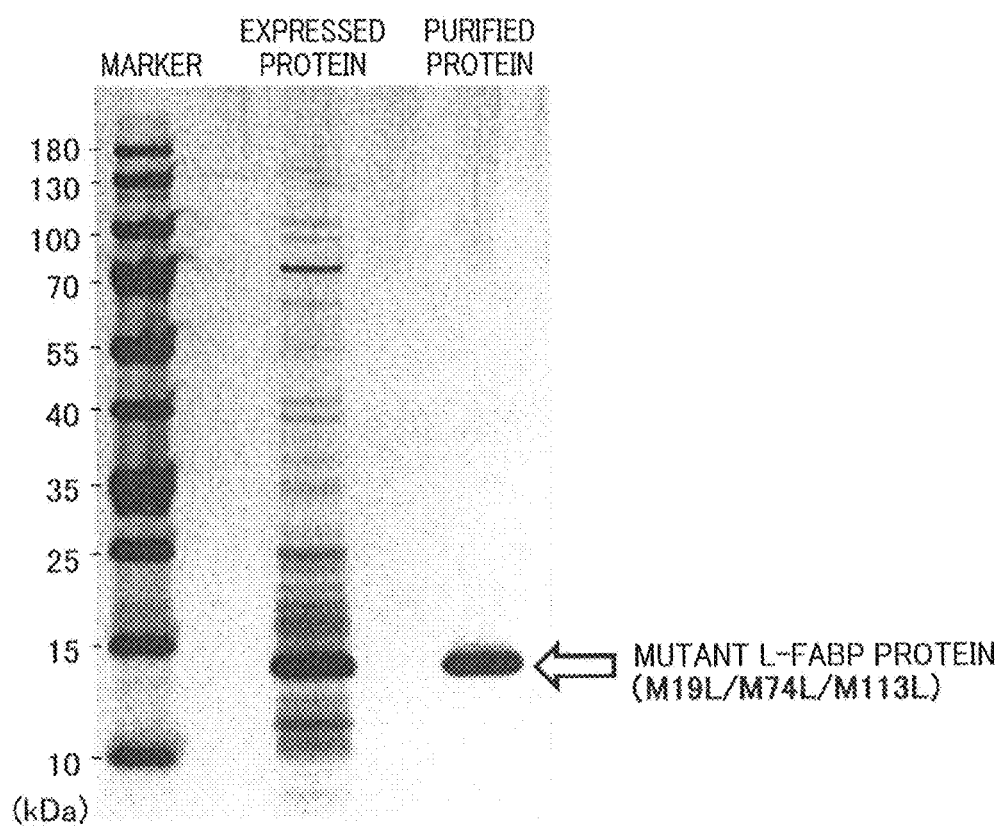
FIG. 7 is a diagram showing L-FABP M19L/M74L/M113L and purified protein expressed by CORYNEX (registered trademark).

L-FABP M19L/M74L/M113L and the like that had been expressed by the method described above were first subjected to buffer exchange with buffer A (10 mM Tris-HCl (pH 8.5) and 1 mM DTT) using a centrifuge type filter unit, AMICON (registered trademark) Ultra-15, 3 kDa (manufactured by Millipore Corp.). Next, purification was performed using a HiTrapQ FF column, 5 mL (manufactured by GE Healthcare, Inc.). L-FABP M19L/M74L/M113L that had adsorbed to the HiTrapQ FF column was washed with buffer A, subsequently elution was performed by a linear concentration gradient method using buffer A and buffer B (10 mM Tris-HCl (pH 8.5), 1 mM DTT, and 2 M NaCl), and a fraction containing a peak at which buffer B became 3.1% was collected. The protein thus collected was subjected to protein staining with SDS-PAGE and Silver Stain II Kit Wako (manufactured by Wako Pure Chemical Industries, Ltd.), and the degree of purification was checked. The purification results for L-FABP M19L/M74L/M113L are shown in FIG. 7.

L-FABP M19L/M74L/M113L and the like obtained by the above-described operation were stored at −80° C.

Figure 8:
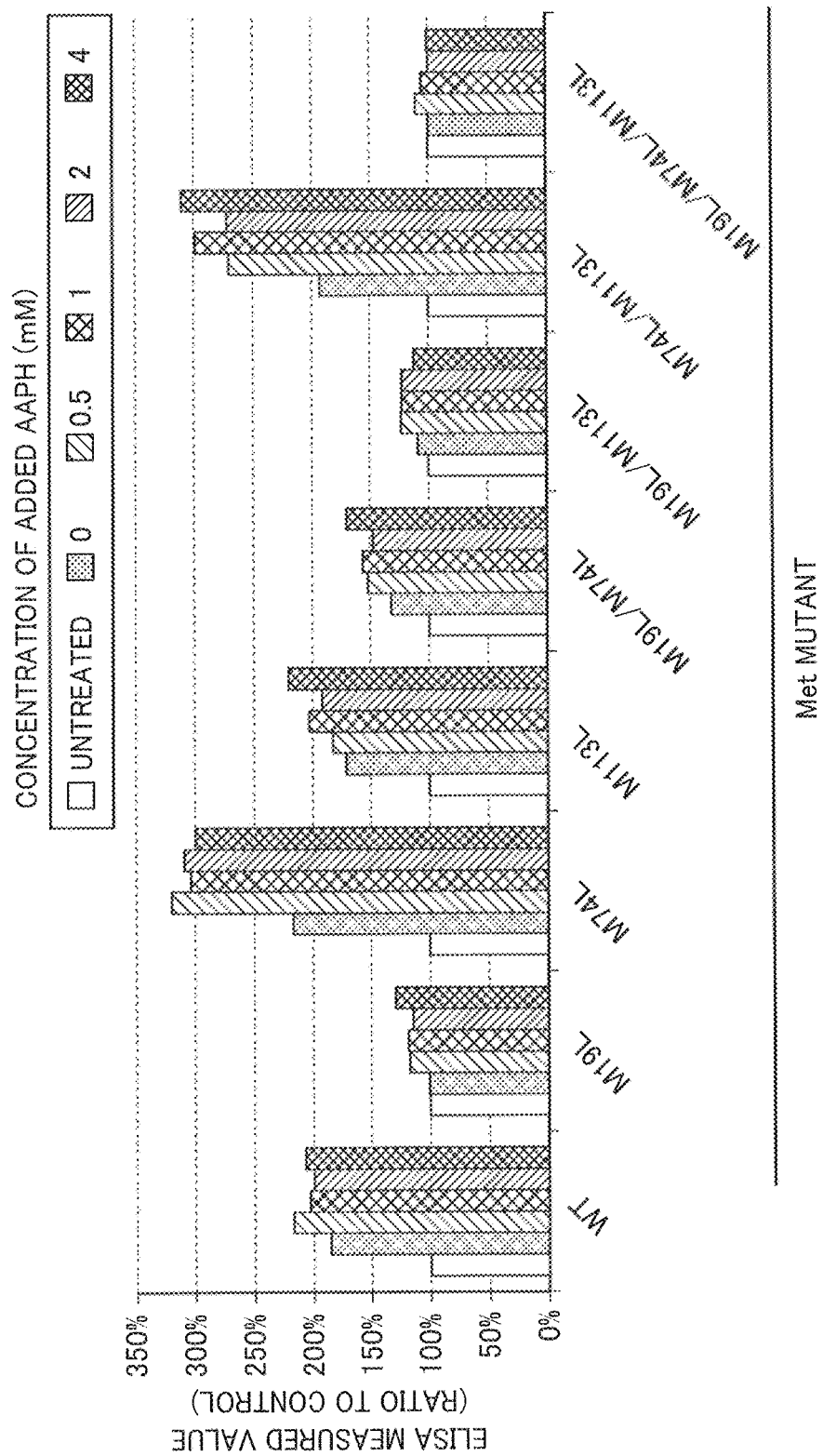
FIG. 8 is a diagram showing the changes in the ELISA measured value of a mutant L-FABP protein caused by AAPH treatment at various concentrations (proportions (%) obtainable by designating the measured value obtained without treatment as 100).

AAPH was added to L-FABP protein solutions (respective solutions of L-FABP M19L, L-FABP M74L, L-FABP M113L, L-FABP M19L/M74L, L-FABP M19L/M113L, L-FABP M74L/M113L, and L-FABP M19L/M74L/M113L) so as to obtain predetermined final concentrations (0 mM, 0.5 mM, 1 mM, 2 mM, and 4 mM), the mixtures were allowed to react for one hour at room temperature, and ELISA measurement was performed. Color development (OD 450 nm) of the labeled antibody was compared with an untreated sample. The comparison results are shown in FIG. 8. As is obvious from the results shown in FIG. 8, it was found that the stability against oxidation of L-FABP M19L and L-FABP M74L was enhanced, and it was confirmed that the oxidation ratios of methionine at positions 19 and 113 were dominant. Furthermore, it was understood that L-FABP M19L/M74L/M113L showed the most excellent stability against oxidation. Next, L-FABP M19L/M74L/M113L and the like for which oxidation stability was confirmed were dissolved in the above-mentioned protein preservative buffer solution for long-term storage of samples, and the solutions were stored at −80° C. Hereinafter, the solutions were used in Examples 2, 3, and 8.

Example 2

(Stability Against Oxidation)

AAPH was added to L-FABP M19L/M74L/M113L to a final concentration of 0 to 5 mM in the presence of BSA, and the mixtures were allowed to react for one hour at room temperature. In consideration of the influence of air oxidation, an untreated sample obtained by adding H₂O only to the protein solutions and performing a measurement immediately after addition was used as an object of comparison.

These reaction solutions and the untreated sample were subjected to an ELISA measurement by using "RENAPRO L-FABP test TMB" (manufactured by CMIC HOLDINGS Co., Ltd.), and the color development (OD 450 nm) of the labeled antibody was compared with the untreated sample. The method of using the diagnostic kit was carried out according to the measurement method based on the attached document that is usually enclosed. The results are presented in FIG. 9.

Figure 9:
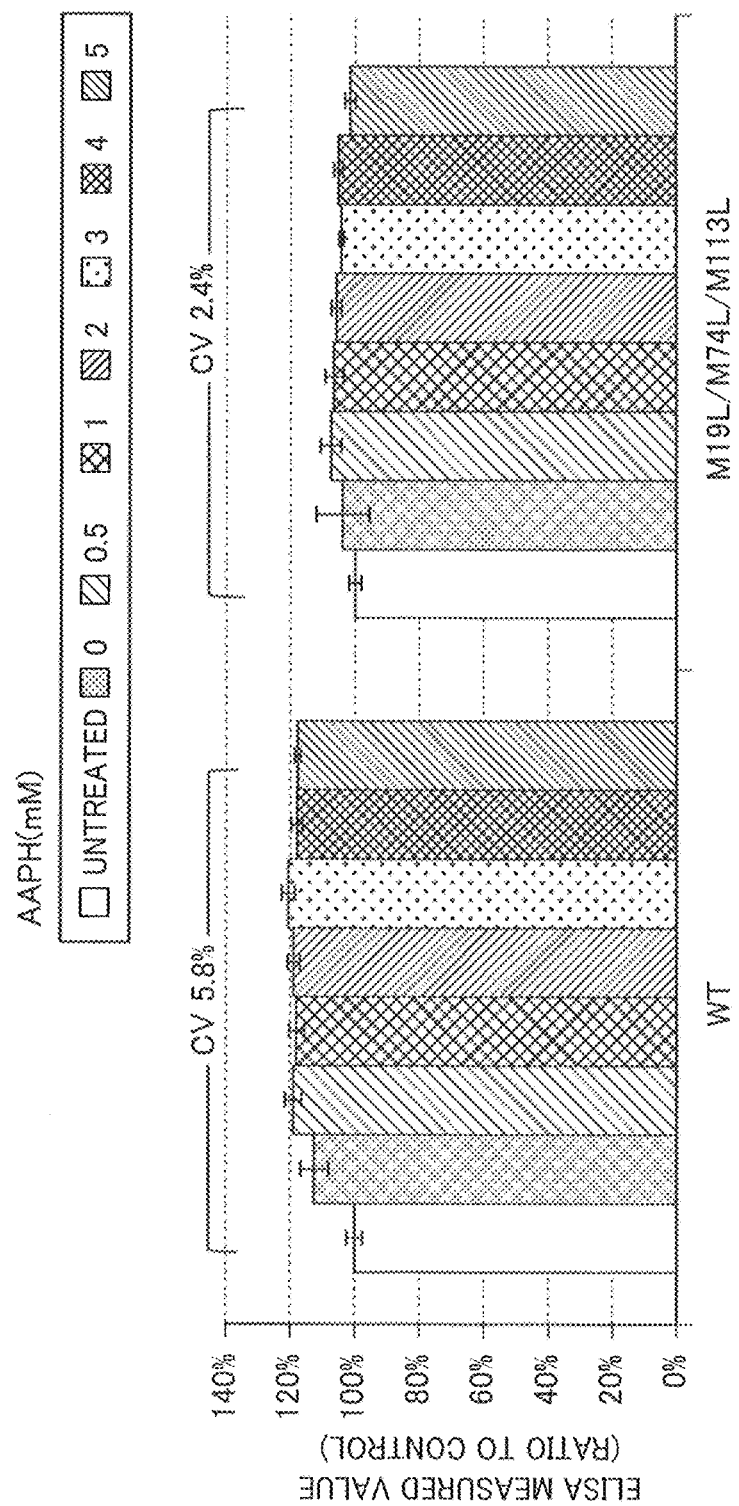
FIG. 9 is a diagram showing the changes in the ELISA measured value of a mutant L-FABP protein caused by AAPH treatment (proportions (%) obtainable by designating the measured value of an untreated sample as 100).

As is obvious from the results of the ELISA measurement shown in FIG. 9, an increase in the measured value of 112% to 121% was confirmed for L-FABP WT, and the coefficient of variation (CV) representing fluctuations was 5.8%. Meanwhile, in the results for L-FABP M19L/M74L/M113L, only an increase of 102% to 107% was recognized, and the CV value was 2.4%. From the results described above, it was clear that the antibody binding capacity of L-FABP M19L/M74L/M113L for AAPH was stable, and the variation in the ELISA measured value was small. That is, it can be said that L-FABP M19L/M74L/M113L was stabilized against an oxidation reaction. Furthermore, the antibody binding capacity of L-FABP WT increased only by leaving the peptide fragment for one hour at room temperature; however, the antibody binding capacity of L-FABP M19L/M74L/M113L did not increase. Therefore, it can be said that the mutant protein was also stabilized against air oxidation.

(Stability at Room Temperature)

In the presence of BSA, L-FABP M19L/M74L/M113L was stored at room temperature (25° C.), and an ELISA measurement was performed according to a conventional method using "RENAPRO L-FABP Test TMB" (manufactured by CMIC HOLDINGS Co., Ltd.) every week for four weeks. A measurement was also performed for the sample stored at −80° C., and this was used as an object of comparison. A comparison was made for the proportion (%) of the color development (OD 450 nm) of the labeled antibody of the sample stored at room temperature with respect to the color development (OD 450 nm) of the labeled antibody of the sample stored at −80° C. designated as 100. The results are presented in FIG. 10.

Figure 10:
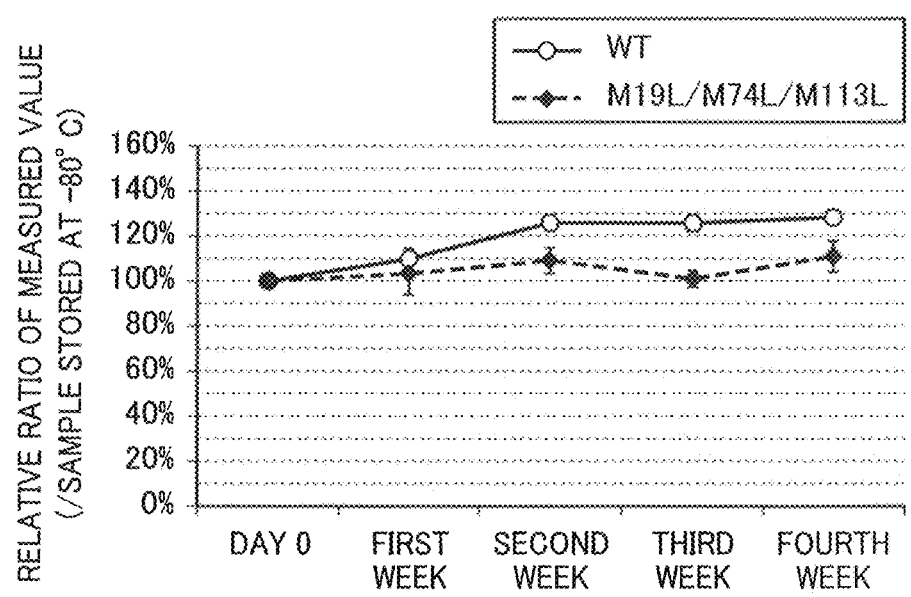
FIG. 10 is a diagram showing the changes in the ELISA measured value of a mutant L-FABP protein caused by long-term storage at room temperature (25° C.) (proportions (%) obtained by designating the measured value of a sample stored at −80° C. as 100).

As is obvious from the results of the ELISA measurement shown in FIG. 10, an increase in the measured value of 110% to 128% was confirmed in the case of L-FABP WT, and the CV was 10.5%. Meanwhile, for L-FABP M19L/M74L/M113L, only an increase of 101% to 111% was recognized, and the CV was 4.7%. From the above results, it became clear that the antibody binding capacity of L-FABP M19L/M74L/M113L during long-term storage at room temperature was stable, and the variation of the ELISA measured value was small. That is, it can be said that L-FABP M19L/M74L/M113L was stabilized for long-term storage at room temperature.

(Stability at 37° C.)

In the presence of BSA, L-FABP M19L/M74L/M113L was stored at 37° C., and an ELISA measurement was performed according to a conventional method using "RENAPRO L-FABP Test TMB" (manufactured by CMIC HOLDINGS Co., Ltd.) every week for four weeks. A measurement was also performed for the sample stored at −80° C., and this was used as an object of comparison. A comparison was made for the proportion (%) of the color development (OD 450 nm) of the labeled antibody of the sample stored at room temperature with respect to the color development (OD 450 nm) of the labeled antibody of the sample stored at −80° C. designated as 100. The results are presented in FIG. 11.

Figure 11:
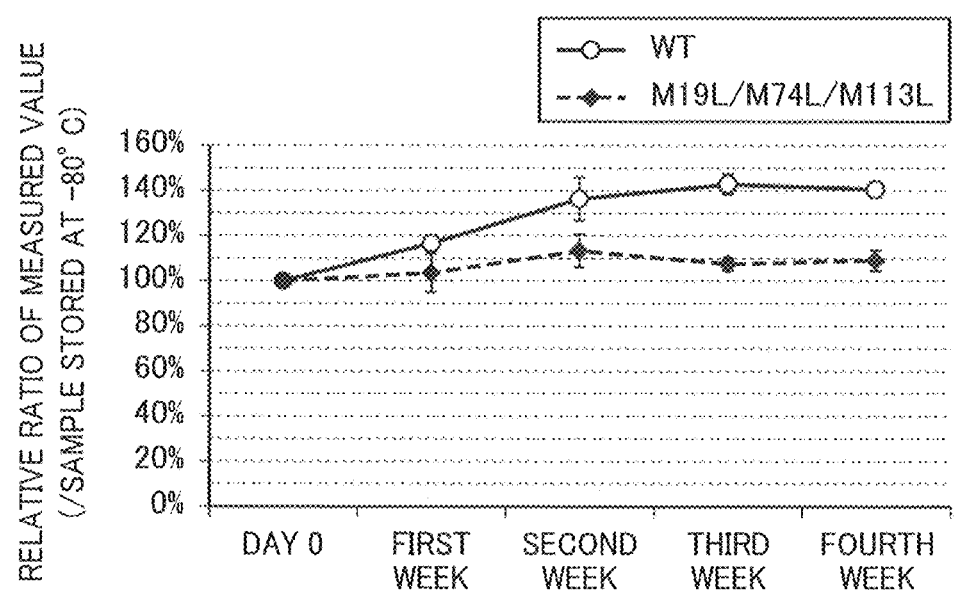
FIG. 11 is a diagram showing the changes in the ELISA measured value of a mutant L-FABP protein caused by long-term storage at 37° C. (proportions (%) obtained by designating the measured value of a sample stored at −80° C. as 100).

As is obvious from the results of the ELISA measurement shown in FIG. 11, an increase in the measured value of 117% to 143% was confirmed for L-FABP WT, and the CV was 14.5%. Meanwhile, only an increase of 104% to 113% was recognized in the case of L-FABP M19L/M74L/M113L, and the CV was 4.8%. From the above results, it became clear that the antibody binding capacity of L-FABP M19L/M74L/M113L during long-term storage at 37° C. was stable, and the variation in the ELISA measured value was small. That is, it can be said that L-FABP M19L/M74L/M113L was stabilized even for long-term storage at 37° C.

Example 3

<Oxidation Stability in ELISA Measurement Using Labeled Antibody Having Recognition Site Different from that of Clone 2>

Figure 12:
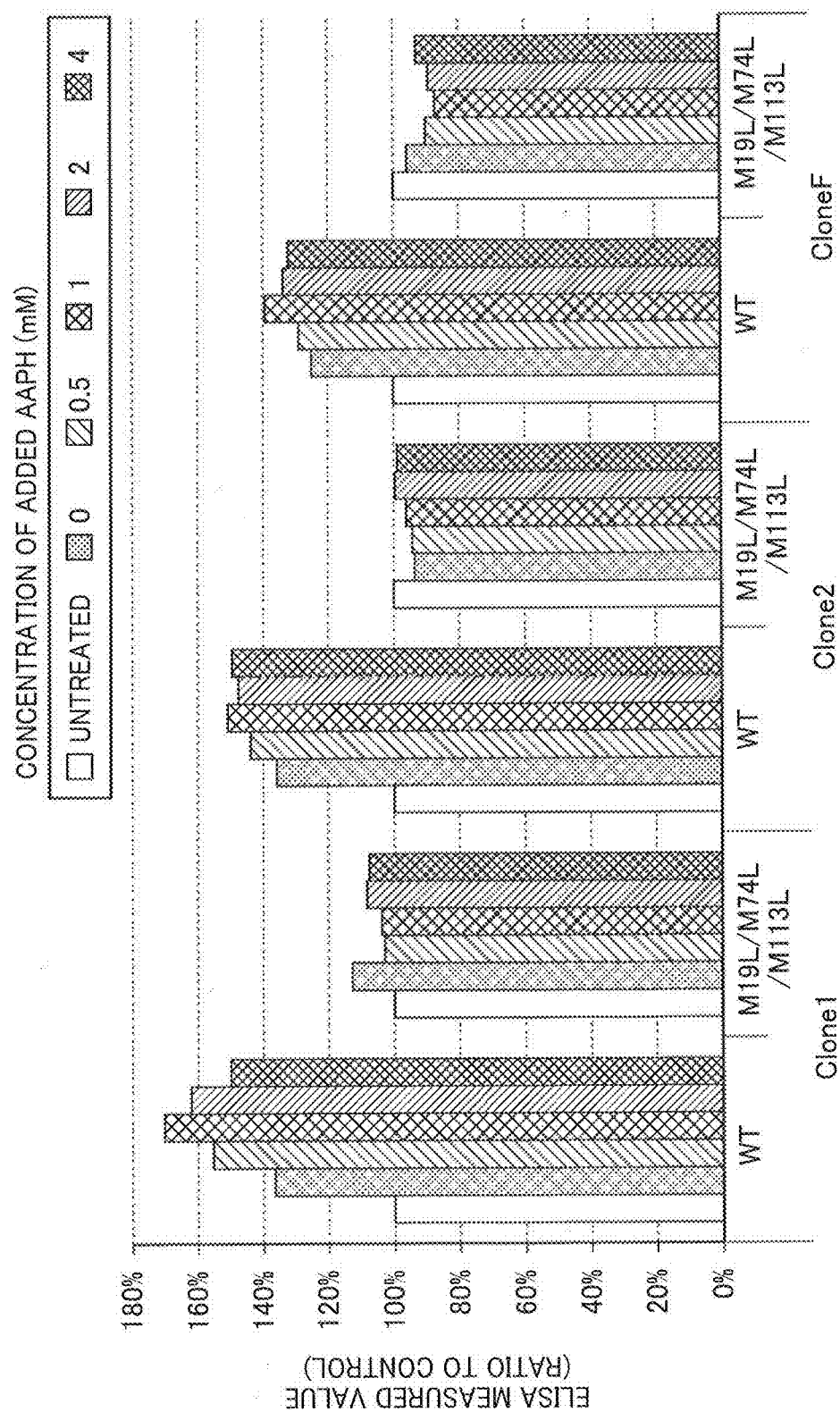
FIG. 12 is a diagram showing the influence of AAPH on ELISA measurement using a labeled antibody having a recognition site different from that of clone 2 (proportions (%) obtainable by designating the measured value of an untreated sample as 100).

AAPH was added to a L-FABP protein solution so as to obtain a predetermined final concentration (0 to 4 mM), and the mixture was allowed to react for one hour at room temperature, and an ELISA measurement was performed. Clone 1, clone 2, and clone F were used as labeled antibodies, and the color development (OD 450 nm) was compared with an untreated sample. The results are shown in FIG. 12. As is obvious from the results shown in FIG. 12, it can be seen that in the method for measuring L-FABP using a labeled antibody based on clone 1 and clone F, the antibody binding capacity of L-FABP WT changes due to oxidation similarly to clone 2, and that changes in the antibody binding capacity caused by oxidation is suppressed in L-FABP M19L/M74L/M113L. Therefore, an L-FABP protein stabilized also for the ELISA measurement system based on anti-L-FABP antibody clone 1 and anti-L-FABP antibody clone F having different antigen recognition sites is effective.

Figure 13:
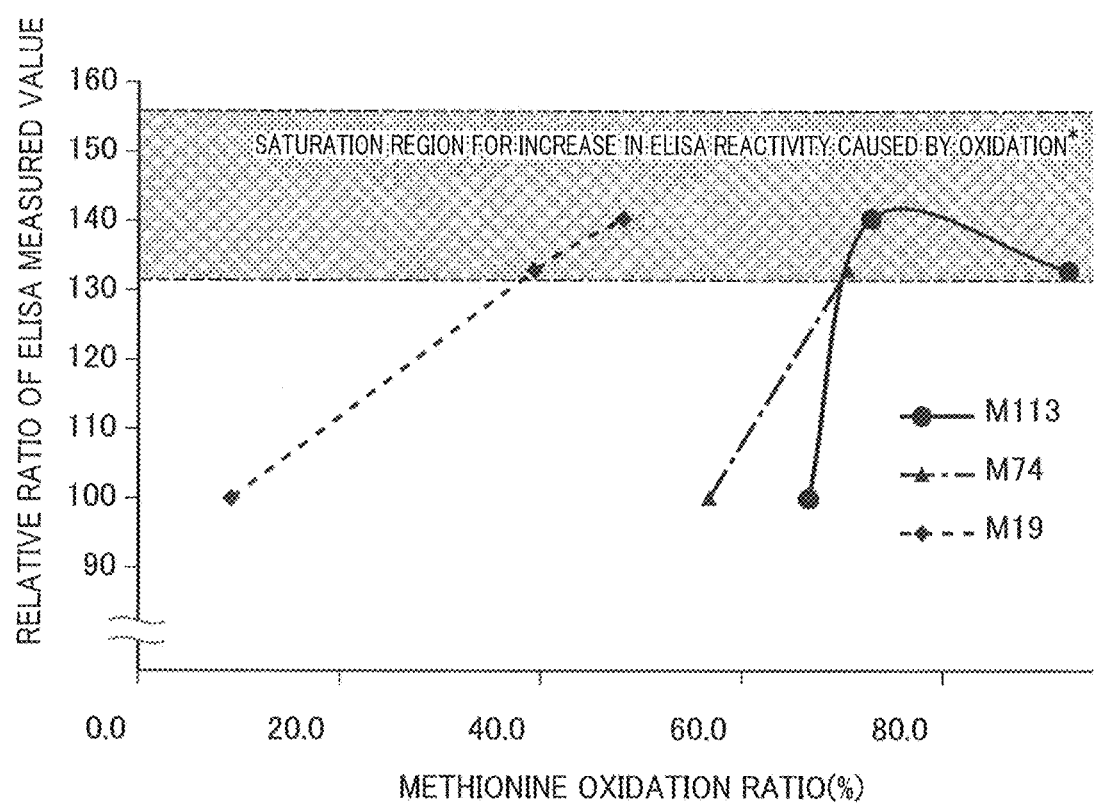
FIG. 13 is a diagram obtained by measuring the respective oxidation ratios of methionines at positions 19, 74, and 113 of various L-FABP proteins showing different degrees of progress in oxidation.

An ELISA measurement was performed in the same manner as in Example 3 by a sandwich ELISA method using the anti-L-FABP antibody clone 2 as a labeled antibody, and the oxidation ratios of methionines at positions 19, 74, and 113 of various L-FABP proteins having different degrees of progress of oxidation were measured. The results are presented in FIG. 13. In FIG. 13, the symbol * is a region in which oxidation is approximately saturated and stabilized based on the data (various data of the concentration with added AAPH) of the ELISA measured value of WT L-FABP using clone 2 shown in Example 3 and FIG. 12, and the ELISA measured value is in the range of the average value±2SD (standard deviation), is referred to as "saturation region of ELISA reactivity increase caused by oxidation". As can be seen from FIG. 13, the minimum oxidation ratio in the region in which oxidation is approximately saturated and stabilized was about 38% for methionine at position 19, the minimum oxidation ratio was about 70% for methionine at position 74, and the minimum oxidation ratio was about 73% for methionine at position 113. From the results described above, it can be said that when methionine at position 19 has an oxidation ratio of 30% or higher, this contributes to narrowing of the variation range of the ELISA measured value. Furthermore, it can also be said that methionine at position 113 having an oxidation ratio of 70% or higher also contributes to narrowing of the variation range of the ELISA measured value. From the results shown in FIG. 13, it can be expected that also for methionine at position 74, the increase in the ELISA measured value in the "saturation region for increase in ELISA reactivity caused by oxidation" in FIG. 13 is saturated.

Example 4

<Stability at 37° C. of Oxidation-Treated L-FABP Standard>

L-FABP that had been oxidation-treated with 40 mM AAPH was stored at 37° C., and an ELISA measurement was performed according to a conventional method using "RENAPRO L-FABP Test TMB" every week for two weeks. A measurement was also made for the sample that had been stored at 4° C., and this was used as an object of comparison. A comparison was made for the proportion (%) of the color development (OD 450 nm) of the labeled antibody of the sample stored at 37° C. with respect to the color development (OD 450 nm) of the labeled antibody of the sample stored at 4° C. designated as 100. The results are presented in FIG. 14.

Figure 14:
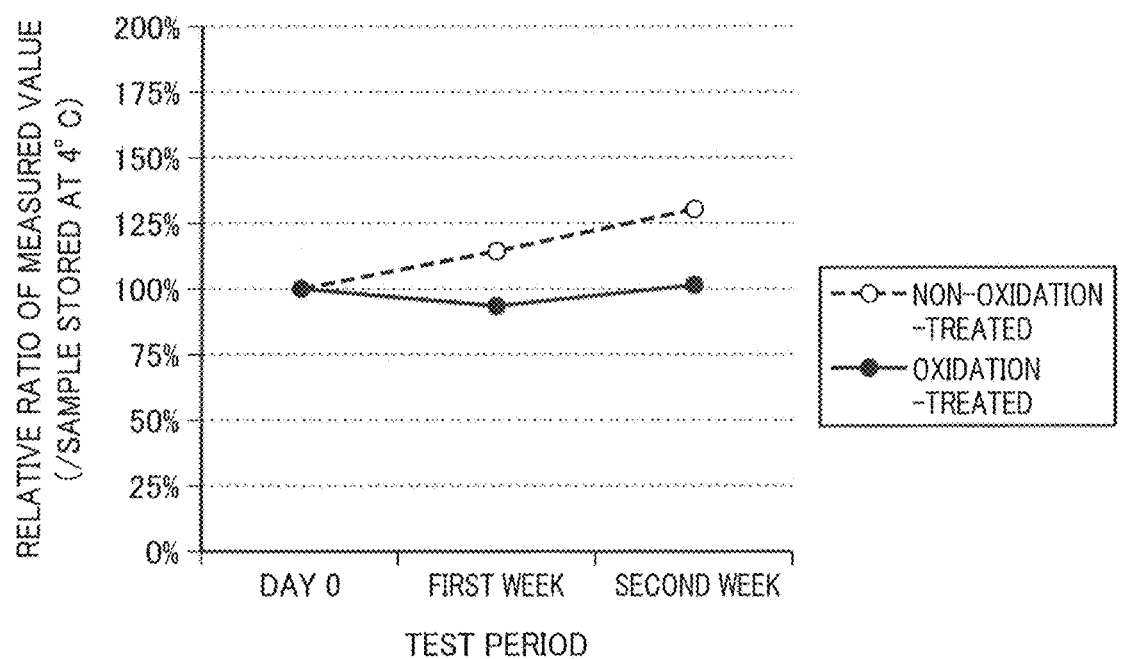
FIG. 14 is a diagram showing the changes in the ELISA measured value of oxidized L-FABP protein caused by storage for two weeks at 37° C. (proportions (%) obtained by designating the measured value of a sample stored at 4° C. as 100).

As is obvious from the results of the ELISA measurement as shown in FIG. 14, in the case of L-FABP that had been oxidation-treated, only an increase of 94% to 102% was recognized. Meanwhile, in the case of L-FABP that was not oxidized, an increase of 114 to 130% was recognized. From the results described above, it became clear that the antibody binding capacity of oxidized L-FABP during long-term storage at 37° C. was stable, and the variation in the ELISA measured value was small. That is, it can be said that L-FABP that had been oxidation-treated is stabilized even for long-term storage at 37° C.

Example 5

<Stability Obtained by Addition of Fatty Acid>

Figure 15A:
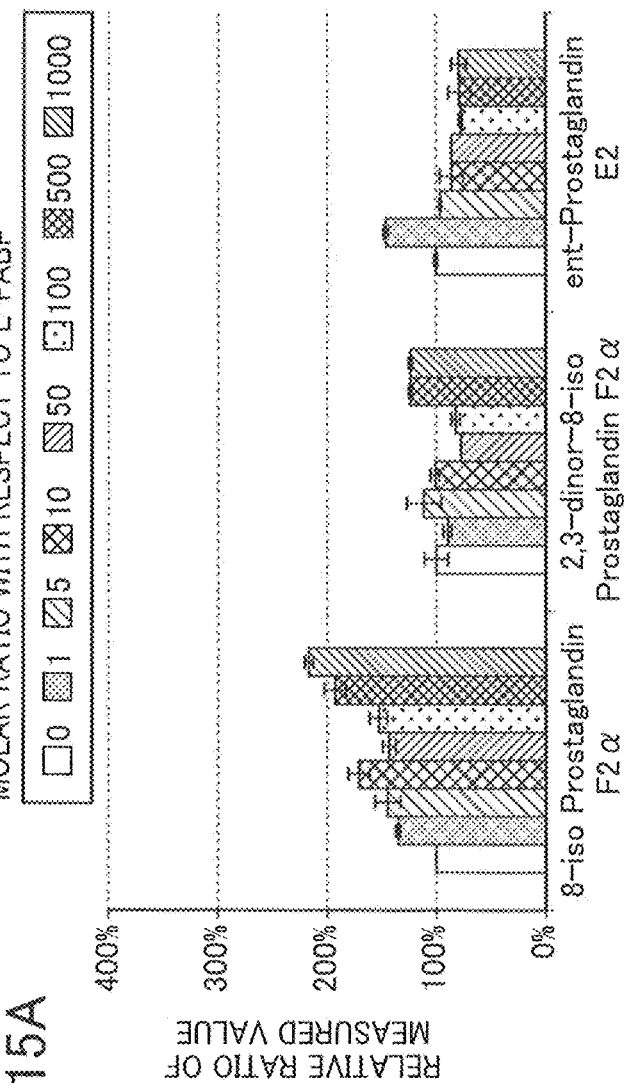
FIG. 15(a) is a diagram showing the changes in the ELISA measured value caused by various fatty acids at various concentrations (proportions (%) obtained by designating zero-fold molar amount of the amount of addition of fatty acid as 100)
Figure 15B:
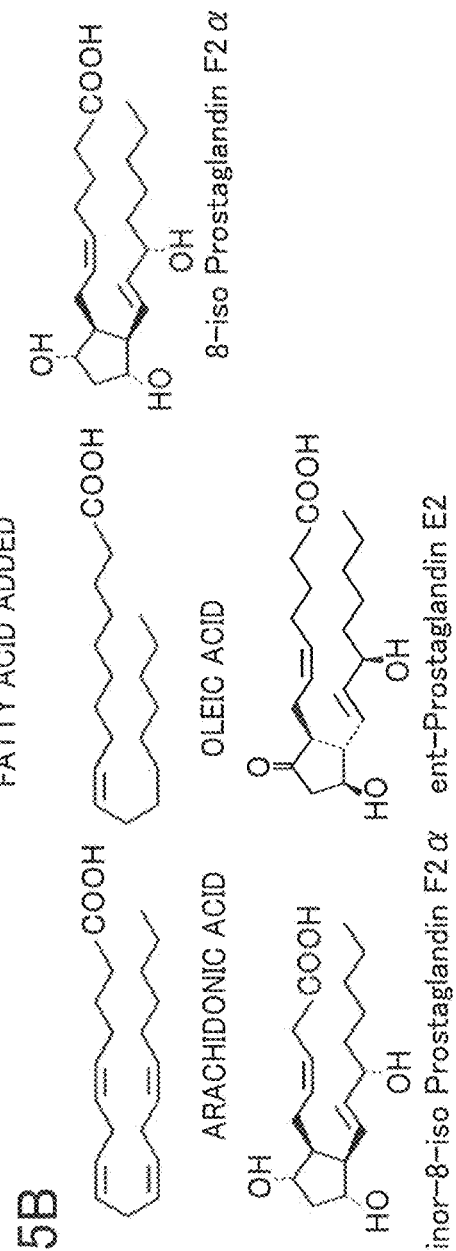
FIG. 15(b) is a diagram showing the type of the various fatty acids.

FIG. 15(a) is a diagram showing the changes in the ELISA measured value of L-FABP protein caused by a fatty acid addition treatment (proportions (%) obtained by designating the measured value of fatty acid addition in a zero-fold amount as 100). It became clear that the antibody binding capacity of L-FABP protein is changed by the type (FIG. 15(b)) or concentration of the binding fatty acid. FIG. 15(a) shows changes in the antibody binding capacities of 8-iso-prostaglandin $F_{2\alpha}$, 2,3-dinor-8-iso-prostaglandin $F_{2\alpha}$, and enta-prostaglandin $E_2$ to the L-FABP protein. Explanation on arachidonic acid and oleic acid will be given below.

Next, various fatty acids were added to wild type L-FABP protein (L-FABP WT) or L-FABP M19L/M74L/M113L such that the final molar amount of each fatty acid would be 200,000 times the molar amount of the protein, and the mixtures were allowed to react for 1.5 hours at room temperature. Furthermore, in consideration of the influence of air oxidation, an untreated sample obtained by adding only DMSO (final concentration 5%) to the protein solutions and performing measurement immediately after the addition was used as a sample as an object of comparison.

These reaction solutions and the untreated sample were subjected to ELISA measurement using "RENAPRO L-FABP Test TMB" in the presence of 1 mass % of BSA, and the color development (OD 450 nm) of the labeled antibody was compared with that of the untreated sample. The method of using the diagnostic kit was carried out according to the measurement method based on the attached document that is usually attached. The results are presented in FIG. 16(a) to FIG. 16(c).

Figure 16A:
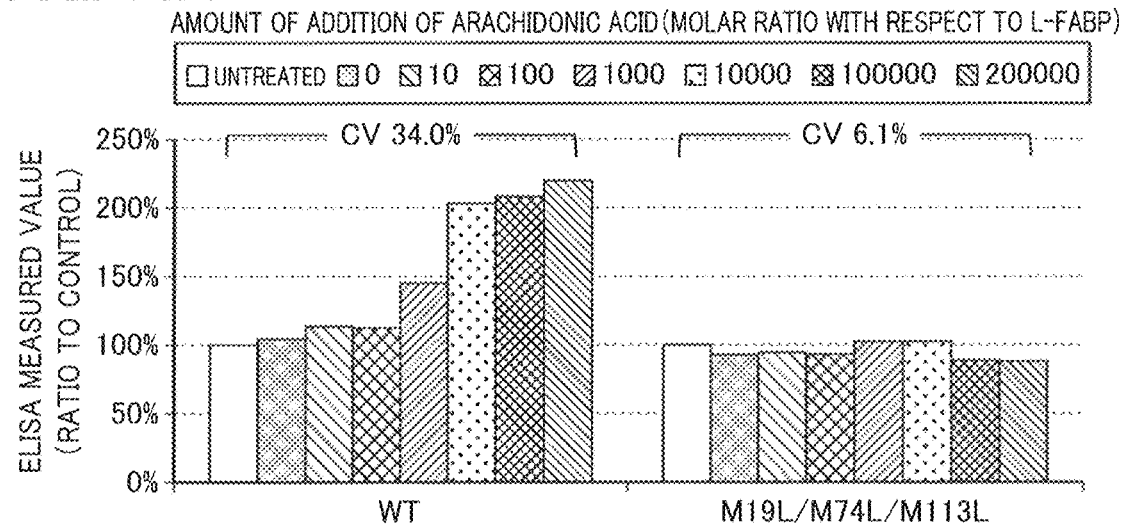
FIG. 16 is a diagram showing the changes of the ELISA measured value of a mutant L-FABP protein caused by a fatty acid addition treatment (proportions (%) obtained by designating the measured value of an untreated sample as 100).
Figure 16B:
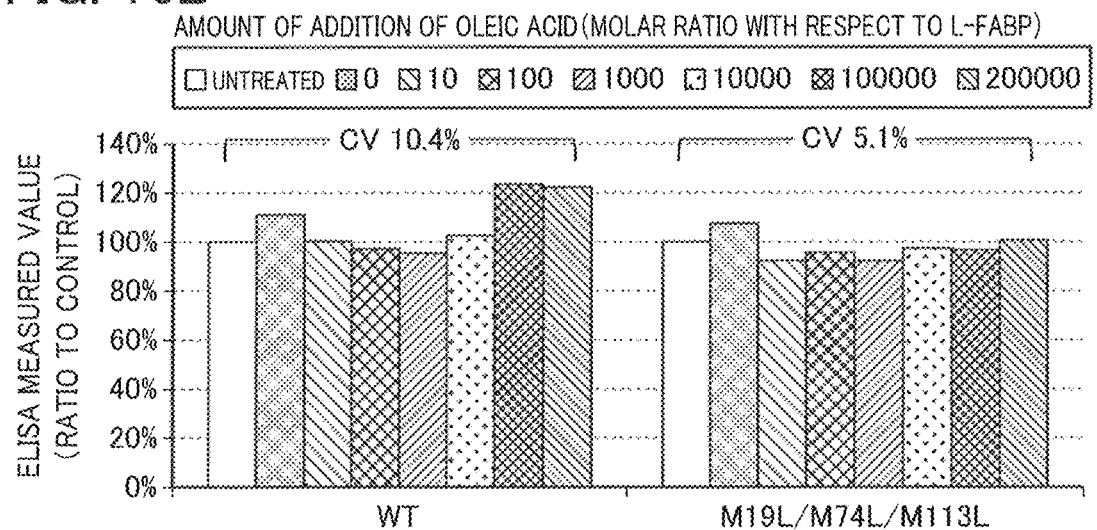
Figure 16C:
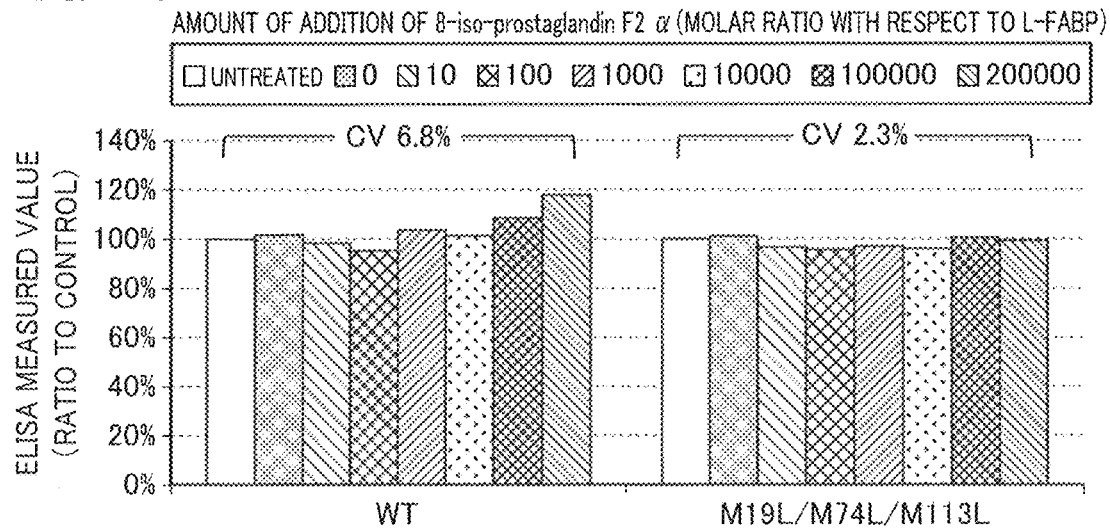

FIG. 16(a) is a diagram showing the changes in the ELISA measured value caused by addition of arachidonic acid at various concentrations; FIG. 16(b) is a diagram showing the changes in the ELISA measured value caused by addition of oleic acid at various concentrations; and FIG. 16(c) is a diagram showing the changes in the ELISA measured value caused by addition of 8-iso-prostaglandin $F_{2\alpha}$ at various concentrations. As is obvious from the results of ELISA measurement shown in FIG. 16(a) to FIG. 16(c), in the case of L-FABP WT, an increase in the measured value of 104% to 220% (CV 34.0%) was confirmed with regard to arachidonic acid, an increase in the measured value of 100% to 124% (CV 10.4%) was confirmed with regard to oleic acid, and variations in the measured value of 95% to 118% (CV 6.8%) were confirmed with regard to 8-iso-prostaglandin $F_{2\alpha}$. On the other hand, in the case of L-FABP M19L/M74L/M113L, variations in the measured value of 88% to 103% (CV 6.1%) were confirmed with regard to arachidonic acid, variations in the measured value of 92% to 107% (CV 5.1%) were confirmed with regard to oleic acid, and an increase in the measured value of 96% to 101% (CV 2.3%) was confirmed with regard to 8-iso-prostaglandin $F_{2\alpha}$. From the results shown in FIG. 16, it can be seen that as more fatty acid is added to L-FABP WT, the change in the ELISA measured value approaches saturation, and thus, the variation range of the ELISA measured value can be regulated by using a liver-type fatty acid-binding protein containing a particular amount or more of a fatty acid as a standard.

In particular, it can be seen from the results shown in FIG. 16(a), when arachidonic acid is incorporated, the change in the ELISA measured value approaches saturation with a relatively small molar amount of arachidonic acid. It is speculated that at least a portion of the added fatty acid does not bind to L-FABP WT but adsorb to BSA. Furthermore, it became clear that the antibody binding capacity of L-FABP M19L/M74L/M113L is stable against addition of a fatty acid, and the variation in the ELISA measured value is small. That is, it can be said that L-FABP M19L/M74L/M113L is stabilized against addition of a fatty acid.

Example 6

<Regulation of Variation in ELISA Measured Value Caused by Binding of Fatty Acid (Arachidonic Acid or Oleic Acid) to L-FABP>

Figure 17:
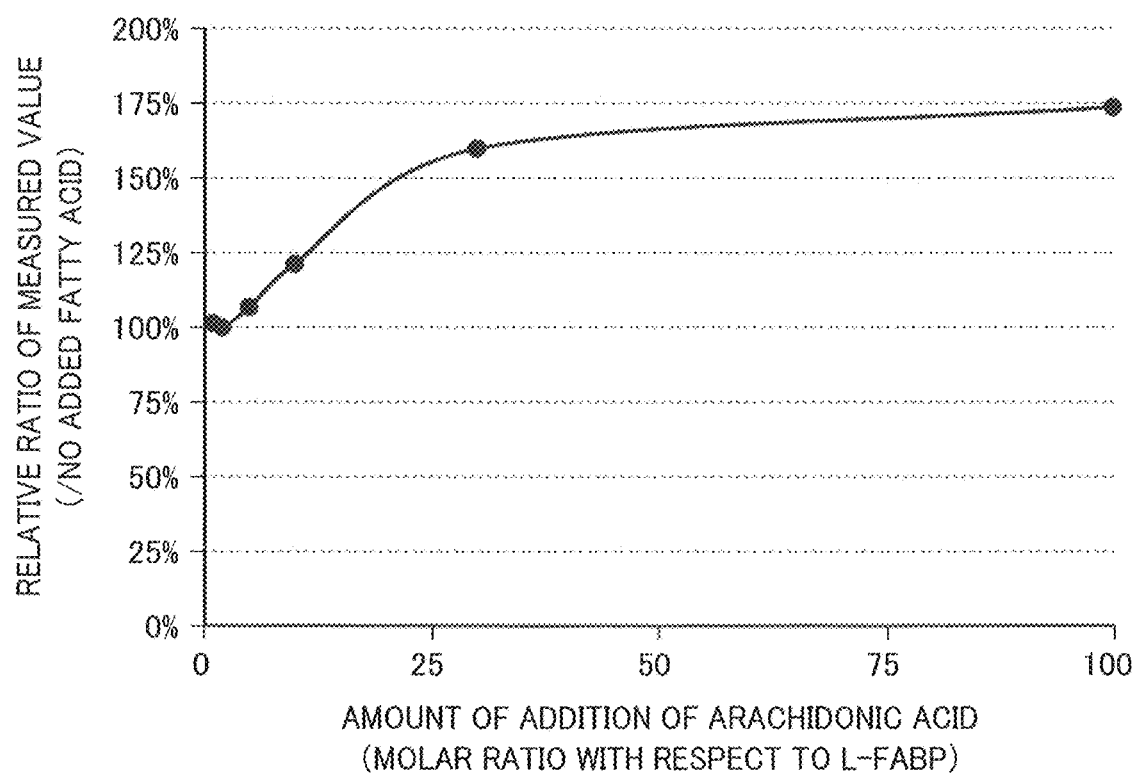
FIG. 17 is a diagram showing the changes in the amount of addition of arachidonic acid and the ELISA measured value (proportions (%) obtained by designating zero-fold molar amount of the amount of addition of arachidonic acid as 100) obtained when arachidonic acid was added in the absence of BSA and then free arachidonic acid was removed by dialysis.
Figure 18:
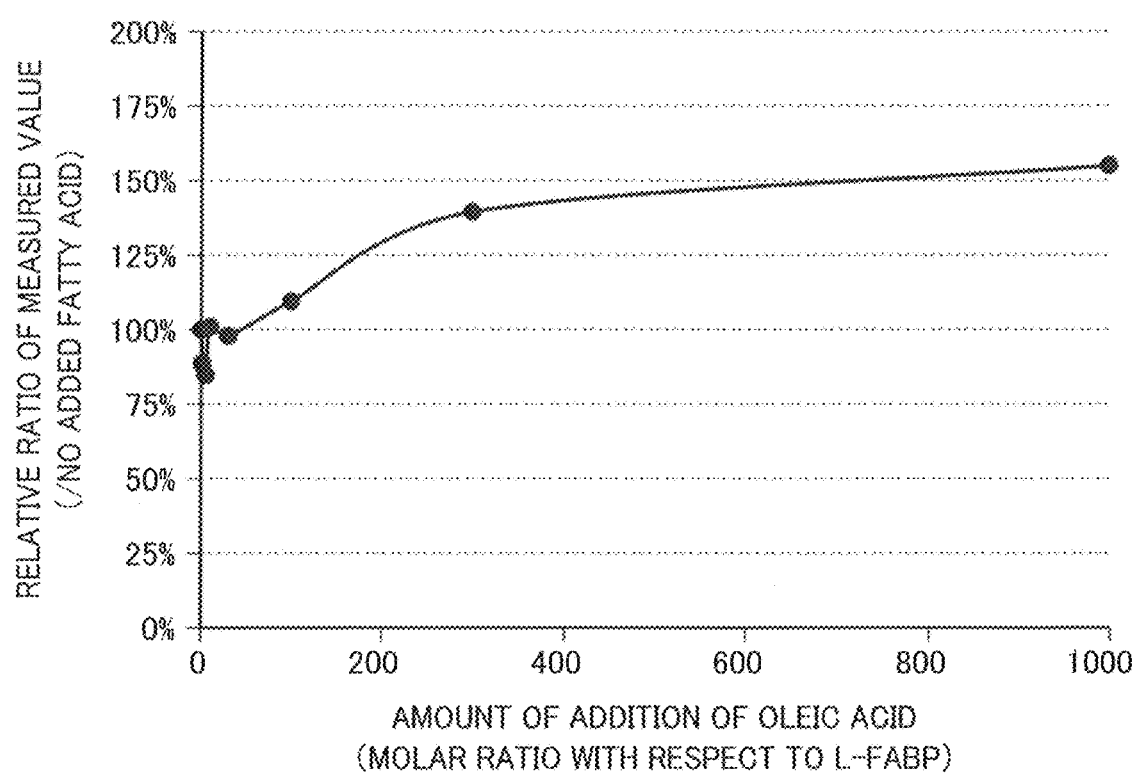
FIG. 18 is a diagram showing the changes in the amount of addition of oleic acid and the ELISA measured value (proportions (%) obtained by designating zero-fold molar amount of the amount of addition of oleic acid as 100) obtained when oleic acid was added in the absence of BSA and then free oleic acid was removed by dialysis.

FIG. 17 and FIG. 18 are diagrams showing the amount of addition of a fatty acid (arachidonic acid or oleic acid) and the changes in the ELISA measured value (proportions (%) obtained by designating a zero-fold molar amount of the amount of addition of the fatty acid as 100). In the absence of BSA, a fatty acid (arachidonic acid or oleic acid) was added to L-FABP in a 0-fold to 100-fold molar amount, the mixtures were allowed to react for 60 minutes at room temperature, and then the mixture was dialyzed overnight against physiological saline. The next day, the dialysis outer liquid was exchanged, and dialysis was performed again overnight. Thus, free fatty acid that was not bound to L-FABP was removed. The changes in the ELISA measured value of the samples thus obtained (proportions (%) obtained by designating a zero-fold molar amount of the amount of addition of the fatty acid as 100) are shown in FIG. 17 and FIG. 18. As is obvious from FIG. 17, it was confirmed that the changes in the ELISA measured value caused by addition of arachidonic acid became constant when the fatty acid was added in a molar amount 10 times or more the molar amount of L-FABP, and the changes became more constant when arachidonic acid was added in a molar amount 30 times or more the amount of the protein. Furthermore, as is obvious from FIG. 18, it was confirmed that the changes in the ELISA measured value caused by addition of oleic acid became constant when the fatty acid was added in a molar amount 100 times or more the molar amount of L-FABP, and the changes became more constant when oleic acid was added in a molar amount 300 times or more the molar amount of the protein.

Example 7

<Stability at 37° C. of L-FABP Standard Bound with Arachidonic Acid or Oleic Acid>

A sample produced by incorporating arachidonic acid in a molar amount 50 times the molar amount of L-FABP by a method similar to that of Example 6 so as to cause arachidonic acid to be bound to L-FABP, and diluting the L-FABP with a BSA-containing protein preservative buffer solution was used, and the sample was stored by a method similar to that of Example 5. Changes in the ELISA measured value at 37° C. for two weeks were checked. The results are presented in FIG. 19. Similarly, a sample produced by incorporating oleic acid in a molar amount 1,000 times the molar amount of L-FABP so as to cause oleic acid to be bound to L-FABP, and diluting the L-FABP with a BSA-containing protein preservative buffer solution was used, and changes in the ELISA measured value at 37° C. for two weeks were checked by a similar method. The results are presented in FIG. 14.

Figure 19:
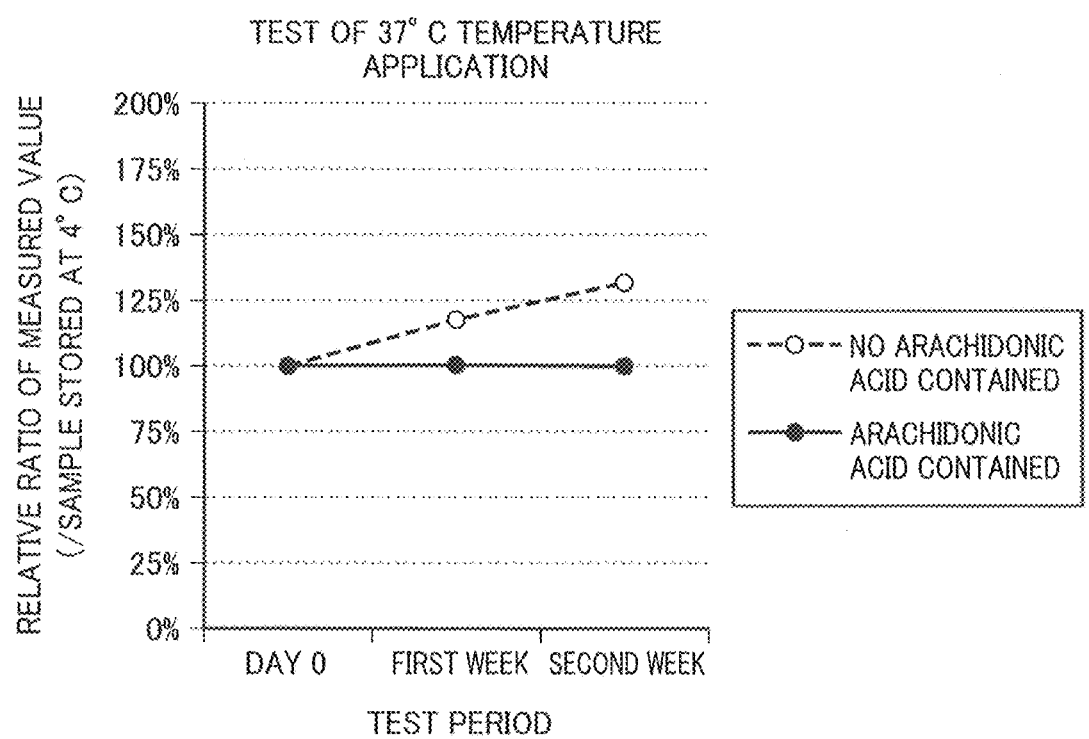
FIG. 19 is a diagram showing the changes in the ELISA measured value of L-FABP protein bound to arachidonic acid caused by storage for two weeks at 37° C. (proportions (%) obtained by designating the measured value of a sample stored at 4° C. as 100), the arachidonic acid-bound protein being obtained by adding arachidonic acid in a 50-fold molar amount in the absence of BSA and then removing free arachidonic acid by dialysis.
Figure 20:
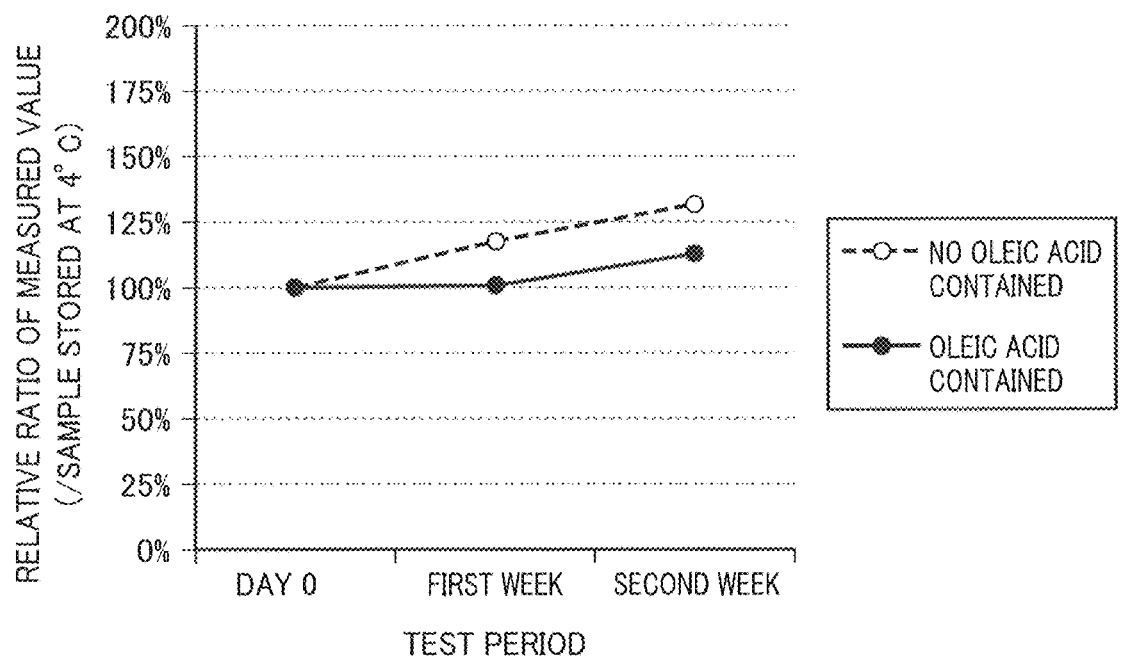
FIG. 20 is a diagram showing the changes in the ELISA measured value of L-FABP protein bound to oleic acid caused by storage for two weeks at 37° C. (proportions (%) obtained by designating the measured value of a sample stored at 4° C. as 100), the oleic acid-bound protein being obtained by adding oleic acid in a 1,000-fold molar amount in the absence of BSA and then removing free oleic acid by dialysis.

As is obvious from the results of ELISA measurement shown in FIG. 19, only a variation of 99.9% to 100.3% was recognized in L-FABP bound to arachidonic acid. Meanwhile, in L-FABP that was not bound to arachidonic acid, an increase of 118% to 132% was recognized. From the above results, it became clear that the antibody binding capacity of L-FABP bound to arachidonic acid was stable during long-term storage at 37° C., and the variation in the ELISA measured value was small. Similarly, as is obvious from the results of the ELISA measurement shown in FIG. 20, only a variation of 100% to 110% was recognized in L-FABP bound to oleic acid. Meanwhile, an increase of 120% to 130% was recognized in L-FABP that was not bound to oleic acid. From the above results, it became clear that the antibody binding capacity of L-FABP bound to oleic acid was stable during long-term storage at 37° C., and the variation in the ELISA measured value was small.

Example 8

<Evaluation of L-FABP Standard Using Coefficient of Change in Oxidation as Index>

Figure 21:
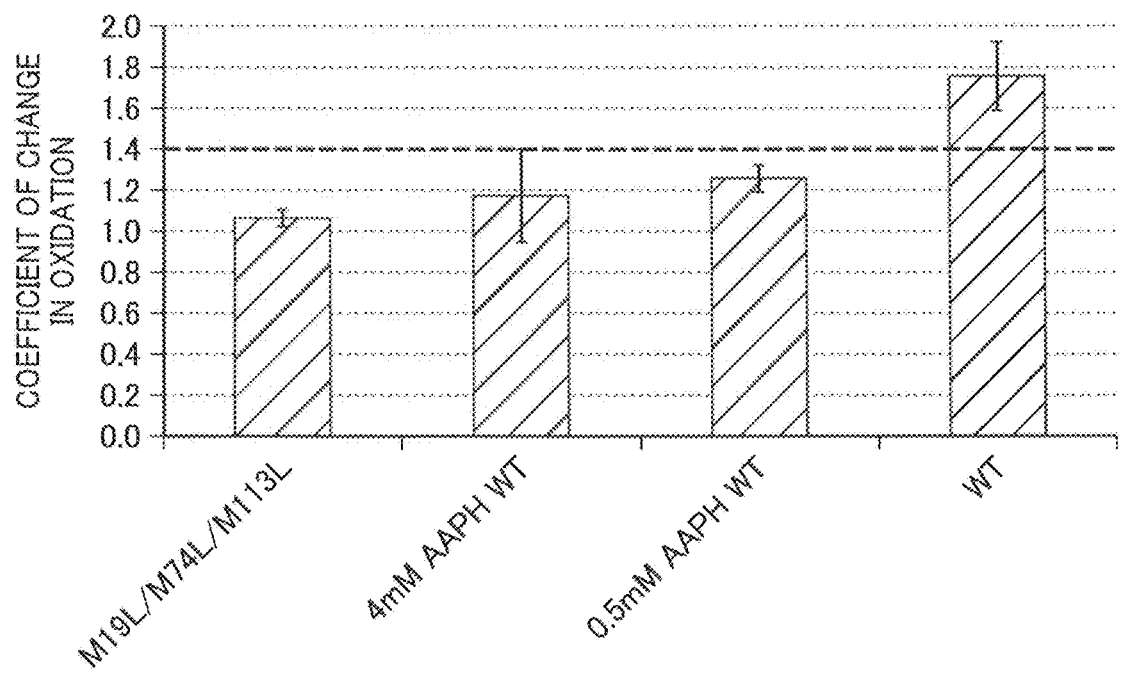
FIG. 21 is a diagram showing the coefficients of variation in oxidation for L-FABP M19L/M74L/M113L, L-FABP WT treated with 0.5 mM or 4 mM AAPH, and L-FABP WT.

In Example 3 and FIG. 12, L-FABP M19L/M74L/M113L that was found to have a small variation in the ELISA measured value, L-FABP WT treated with 0.5 mM AAPH, L-FABP WT treated with 4 mM AAPH, and L-FABP WT were subjected to an oxidation treatment with 10 mM AAPH for one hour at 25° C., and the coefficient of change in oxidation was calculated from the OD ratio of the ELISA measured value in the presence or absence of the oxidation treatment. Furthermore, the coefficient of change in oxidation was also calculated for L-FABP WT as a control. The results are presented in FIG. 21. As is obvious from the results shown in FIG. 21, the coefficient of change in oxidation of L-FABP WT as a control was about 1.8. Meanwhile, regarding L-FABP M19L/M74L/M113L that was found to have a small variation in the ELISA measured value, L-FABP WT treated with 0.5 mM AAPH, and L-FABP WT treated with 4 mM AAPH shown in Example 3 and FIG. 12, the coefficient of change in oxidation was 1.3 or less in all cases. Thus, when the coefficients of variation in oxidation of L-FABP M19L/M74L/M113L, L-FABP WT treated with 0.5 mM AAPH, and L-FABP WT treated with 4 mM AAPH were 1.4 (1.2+0.2) or less, which was the average value+2SD (standard deviation), it can be said that the variation in the measured value against oxidation is regulated, and the protein is stable.

Figure 22:
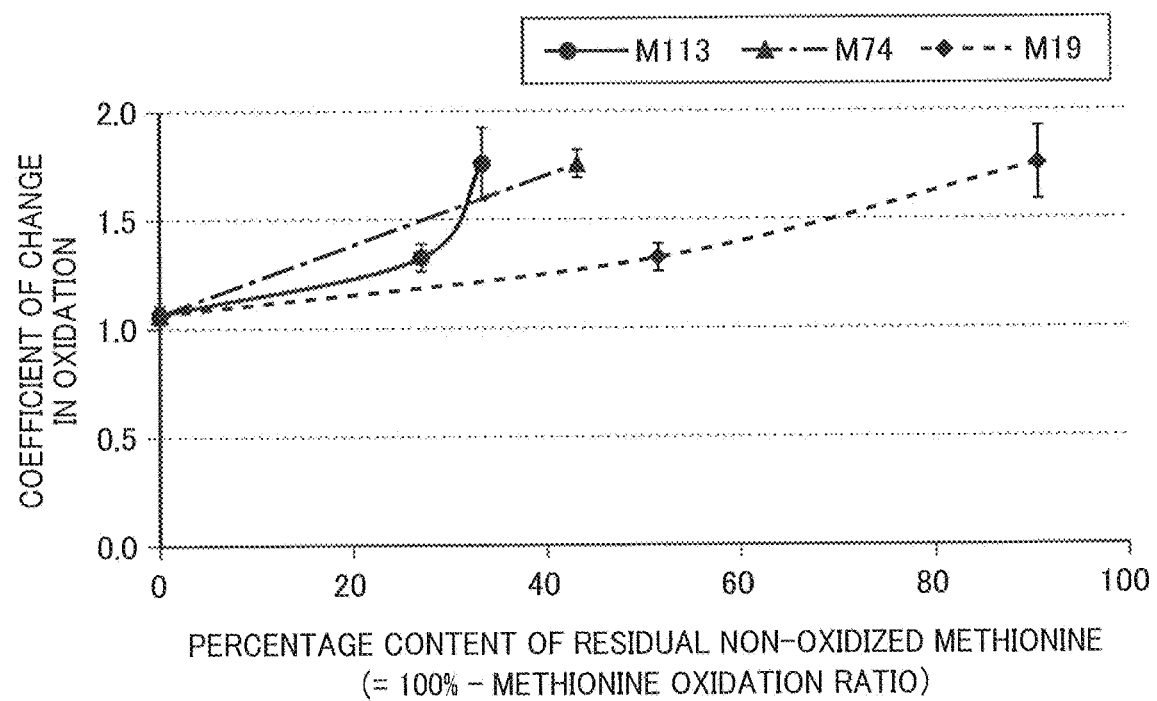
FIG. 22 is a diagram showing the correlation between the percentage content of residual non-oxidized methionine and the coefficient of change in oxidation for each of the methionines at positions 19, 74, and 113.

Next, various L-FABP proteins having different degrees of progress of oxidation used in Example 3 and FIG. 13 were respectively subjected to an oxidation treatment using 10 mM AAPH for one hour at 25° C., and the coefficients of variation in oxidation were calculated from the OD ratios of the ELISA measured values in the presence or absence of the oxidation treatment. Subsequently, for each of methionines at positions 19, 74, and 113, the correlation between the methionine oxidation ratio and the coefficient of change in oxidation was calculated as a correlation between the percentage content of residual non-oxidized methionine (100%–methionine oxidation ratio) and the coefficient of change in oxidation. The results are presented in FIG. 22. As is obvious from the results shown in FIG. 22, regarding methionine at position 19, the percentage content of residual non-oxidized methionine is less than 70% (that is, the oxidation ratio was 30% or higher), and the coefficient of change in oxidation converges. Thus, it can be seen that oxidation variation is regulated. Particularly, when the coefficient of change in oxidation is 1.4 or less, the percentage content of residual non-oxidized methionine is less than 62% (that is, the oxidation ratio is 38% or higher). Thus, it can be said that regulation of variation in oxidation is particularly excellent.

Regarding methionine at position 74, the percentage content of residual non-oxidized methionine is less than 30% (that is, the oxidation ratio is 70% or higher), and the coefficient of change in oxidation converges. Thus, it can be seen that oxidation variation is regulated. Particularly, when the percentage content of residual non-oxidized methionine is less than 25% (that is, the oxidation ratio is 75% or higher), where the coefficient of change in oxidation is 1.4 or less, it can be said that especially excellent regulation of variation in oxidation is achieved. Furthermore, also for methionine at position 113, the percentage content of residual non-oxidized methionine is less than 30% (that is, the oxidation ratio is 70% or higher), and the coefficient of change in oxidation converges. Thus, it can be seen that oxidation variation is regulated.

Figure 23:
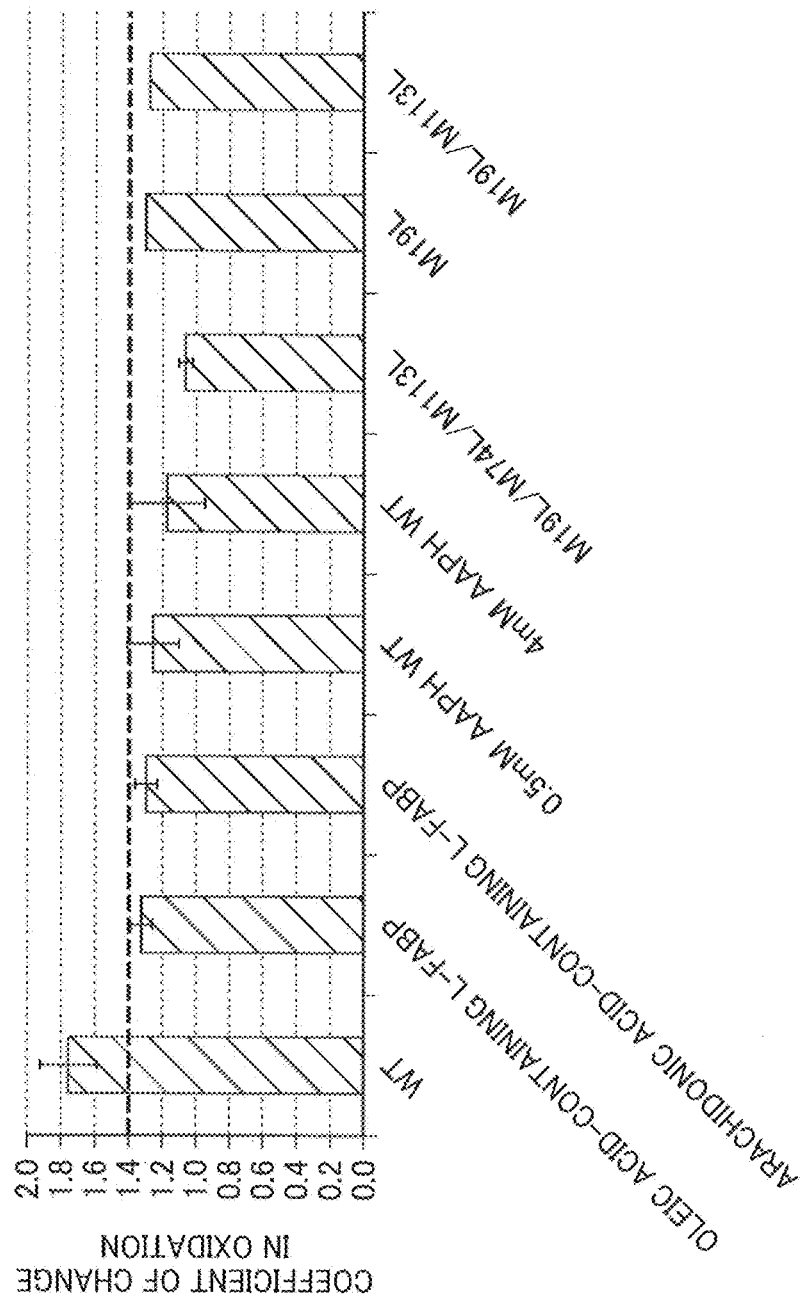
FIG. 23 is a diagram showing the calculation results for the coefficients of variation in oxidation of various L-FABP's.
Figure 24:
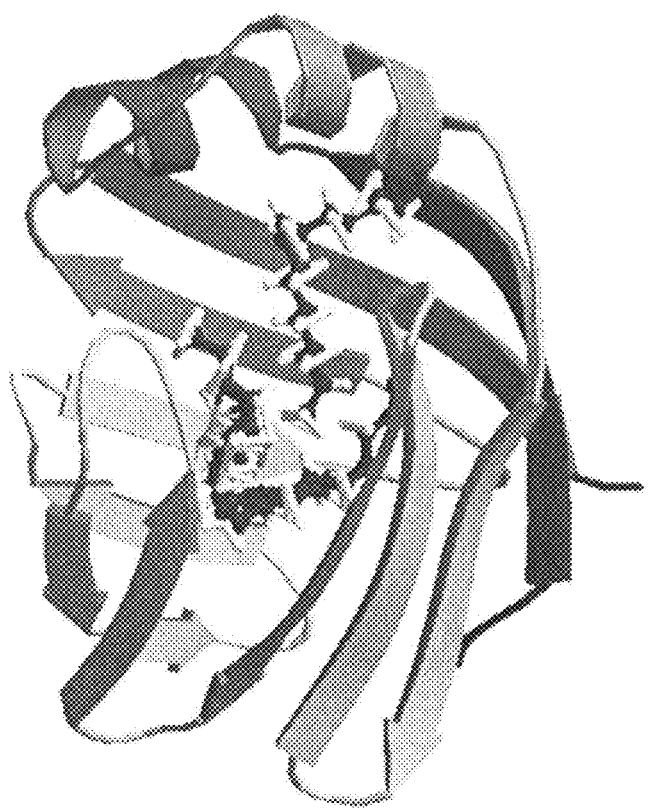
FIG. 24 is a diagram showing a steric structure model showing the binding of L-FABP protein to a free fatty acid.

Furthermore, the coefficients of variation in oxidation were calculated for (1) L-FABP WT, (2) oleic acid-containing L-FABP, (3) arachidonic acid-containing L-FABP, (4) L-FABP WT treated with 0.5 mM AAPH, (5) L-FABP WT treated with 4 mM AAPH, and (6) L-FABP M19L/M74L/M113L in Examples 6 and 7, (7) L-FABP M19L, and (8) L-FABP M19L/M113L. The calculation results are presented in FIG. 23. As is obvious from the results shown in FIG. 23, it can be seen that regarding L-FABP WT, the coefficient of change in oxidation significantly exceeds 1.4 (about 1.8) and does not satisfy stability against oxidation as an L-FABP standard. Meanwhile, regarding (2) oleic acid-containing L-FABP, (3) arachidonic acid-containing L-FABP, (4) L-FABP WT treated with 0.5 mM AAPH, (5) L-FABP WT treated with 4 mM AAPH, (6) L-FABP M19L/M74L/M113L, (7) L-FABP M19L, and (8) L-FABP M19L/M113L, it can be seen that the coefficient of change in oxidation is 1.4 or less in all cases, and the proteins have excellent stability against oxidation.

[Sequence Listing Free Text]

SEQ ID NO:1: Amino acid sequence of L-FABP WT

SEQ ID NO:2: Amino acid sequence of L-FABP M19L/M74L/M113L

SEQ ID NO:3: DNA sequence of L-FABP M19L/M74L/M113L

The invention claimed is:

1. A kit comprising a liver-type fatty acid-binding protein standard comprising a recombinant liver-type fatty acid binding protein, wherein the recombinant liver-type fatty acid-binding protein comprises an amino acid sequence having at least 90% sequence identity to the amino acid sequence of SEQ ID NO: 1, wherein one or more methionines at positions 19, 74, and 113 have been substituted by non-polar amino acids other than methionine, and at least methionines at positions corresponding to positions 19 and 74 of the amino acid sequence of SEQ ID NO: 1 have been substituted by non-polar amino acids other than methionine.

2. A kit comprising a liver-type fatty acid-binding protein standard comprising: at least one fatty acid selected from the group consisting of arachidonic acid and oleic acid; and a recombinant liver-type fatty acid-binding protein comprising an amino acid sequence having at least 90% sequence identity to the amino acid sequence of SEQ ID NO: 1, wherein in the recombinant liver-type fatty acid-binding protein, the methionine at the N-terminus is not deleted and the second serine from the N-terminus is not modified, and when the fatty acid is arachidonic acid, the arachidonic acid is present in a molar amount 30 times or more the molar amount of the liver-type fatty acid-binding protein, and when the fatty acid is oleic acid, the oleic acid is present in a molar amount 300 times or more the molar amount of the liver-type fatty acid-binding protein.

3. The kit of claim 1, wherein a variation range of a labeling intensity measured based on specific binding of a substance to the liver-type fatty acid-binding protein is 10% or less before and after storage at 37° C. for 2 weeks, the variation range is expressed in units of % by (a labeling intensity of the liver-type fatty acid-binding protein standard after storage at 37° C. for 2 weeks/a labeling intensity of the liver-type fatty acid-binding protein standard after storage at 4° C. or −80° C. for 2 weeks) (a labeling intensity of the liver-type fatty acid-binding protein standard before storage at 37° C. for 2 weeks/a labeling intensity of the liver-type fatty acid-binding protein standard before storage at 4° C. or −80° C. for 2 weeks)| x 100.

4. A method of evaluating a liver-type fatty acid-binding protein standard, the method comprising:
subjecting the liver-type fatty acid binding protein standard of claim 1 to an oxidation treatment and
comparing the coefficient of change in oxidation represented by the ratio of a measured value obtained from the liver-type fatty acid-binding protein standard with respect to the measured value obtained from a liver-type fatty acid-binding protein standard that has not been subjected to the oxidation treatment.

5. A method of regulating the variation range of a measured value in a measurement from a liver-type fatty acid-binding protein standard, the method comprising:
providing the liver-type fatty acid-binding protein standard of claims 1 and
incorporating at least one fatty acid selected from the group consisting of arachidonic acid, oleic acid, 8-iso-prostaglandin $F_{2\alpha}$, and 2,3-dinor-8-iso-prostaglandin $F_{2\alpha}$ into the liver-type fatty acid-binding protein standard.

6. A method of drawing a calibration curve for a liver-type fatty acid-binding protein the method comprising:
providing the liver-type fatty acid-binding protein standard of claim 1;
drawing a calibration curve based on the intensity of a label and the amount of the liver-type fatty acid-binding protein standard, wherein the intensity of the label is from an absorbance, an enzyme label intensity, fluorescence intensity, ultraviolet intensity, or radiation intensity.

7. The method of claim 6, further comprising quantifying the amount of a liver-type fatty acid-binding protein in a sample from the calibration curve.

8. The kit of claim 2, further comprising an adsorption preventing agent selected from the group consisting of BSA, casein, skimmed milk, and polyethylene glycol.

9. The kit of claim 1, wherein in the recombinant liver-type fatty acid-binding protein, methionine at the N-terminus is not deleted and the second serine from the N-terminus is not modified.

10. The kit of claim 2, wherein the oleic acid is in a molar amount 1000 times or more the molar amount of the liver-type fatty acid-binding protein.

11. The kit of claim 2, wherein the arachidonic acid is in a molar amount 50 times or more the molar amount of the liver-type fatty acid-binding protein.

12. The kit of claim 1, wherein the methionines at positions 19, 74, and 113 have been substituted by non-polar amino acids other than methionine.

13. A method of regulating the variation range of a measured value in a measurement from a liver-type fatty acid-binding protein standard, the method comprising: providing the liver-type fatty acid-binding protein standard of claim 2 and incorporating at least one fatty acid selected from the group consisting of arachidonic acid, oleic acid, 8-iso-prostaglandin $F_{2\alpha}$, and 2,3-dinor-8-iso-prostaglandin $F_{2\alpha}$ into the liver-type fatty acid-binding protein standard.

14. A method of drawing a calibration curve for a liver-type fatty acid-binding protein the method comprising:
providing the liver-type fatty acid-binding protein standard of claim 2;
drawing a calibration curve based on the intensity of a label and the amount of the liver-type fatty acid-binding protein standard, wherein the intensity of the label is from an absorbance, an enzyme label intensity, fluorescence intensity, ultraviolet intensity, or radiation intensity.

* * * * *